(12) United States Patent
Hopkins

(10) Patent No.: US 11,844,698 B2
(45) Date of Patent: Dec. 19, 2023

(54) ADJUSTABLE ORTHOPEDIC CONNECTIONS

(71) Applicant: Zimmer, Inc., Warsaw, IN (US)

(72) Inventor: Andrew Hopkins, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 580 days.

(21) Appl. No.: 16/567,755

(22) Filed: Sep. 11, 2019

(65) Prior Publication Data

US 2020/0000600 A1 Jan. 2, 2020

Related U.S. Application Data

(62) Division of application No. 14/557,763, filed on Dec. 2, 2014, now Pat. No. 10,449,054.

(Continued)

(51) Int. Cl.
*A61B 17/80* (2006.01)
*A61F 2/40* (2006.01)
(Continued)

(52) U.S. Cl.
CPC ........ *A61F 2/4014* (2013.01); *A61B 17/7037* (2013.01); *A61B 17/8052* (2013.01);
(Continued)

(58) Field of Classification Search
CPC .......... A61F 2002/30378; A61F 2/4014; A61F 2002/4018; A61F 2002/30485;
(Continued)

(56) References Cited

U.S. PATENT DOCUMENTS

| 6,045,581 A | 4/2000 | Burkinshaw |
|---|---|---|
| 6,398,815 B1 | 6/2002 | Pope |

(Continued)

FOREIGN PATENT DOCUMENTS

| CN | 1697633 A | 11/2005 |
|---|---|---|
| CN | 102348431 A | 2/2012 |

(Continued)

OTHER PUBLICATIONS

"U.S. Appl. No. 14/557,763, Final Office Action dated Jan. 11, 2018", 11 pgs.

(Continued)

*Primary Examiner* — Brian E Pellegrino
(74) *Attorney, Agent, or Firm* — Schwegman Lundberg & Woessner, P.A.

(57) ABSTRACT

The disclosure includes methods and systems for making orthopedic connections where there is unique adjustability to the connection. Illustratively, one embodiment provides a connecting assembly for connecting a plurality of orthopedic components. Such connecting assemblies can include a first orthopedic component that provides a female bore. Additionally the assembly can include a second orthopedic component that can be or include a male-type connecting member that is positionable in the bore of the first orthopedic component. In one preferred form, the male-type connecting member will be a quasi-spherical member. The quasi-spherical member can include a textured outer surface, e.g., for contacting one or more walls or surfaces in the bore in a fashion that removeably locks or helps to removeably lock or fix the quasi-spherical member in the bore.

18 Claims, 14 Drawing Sheets

Related U.S. Application Data

(60) Provisional application No. 61/910,700, filed on Dec. 2, 2013.

(51) Int. Cl.
*A61B 17/70* (2006.01)
*A61B 17/86* (2006.01)
*A61F 2/30* (2006.01)
*A61F 2/46* (2006.01)
*A61B 17/00* (2006.01)

(52) U.S. Cl.
CPC ........ *A61B 17/8605* (2013.01); *A61F 2/4003* (2013.01); *A61B 2017/00858* (2013.01); *A61F 2002/3028* (2013.01); *A61F 2002/30138* (2013.01); *A61F 2002/30332* (2013.01); *A61F 2002/30378* (2013.01); *A61F 2002/30485* (2013.01); *A61F 2002/30538* (2013.01); *A61F 2002/30604* (2013.01); *A61F 2002/30772* (2013.01); *A61F 2002/30774* (2013.01); *A61F 2002/4037* (2013.01); *A61F 2002/4641* (2013.01)

(58) Field of Classification Search
CPC ............ A61B 17/8052; A61B 17/7208; A61B 17/1728; A61B 17/58; A61B 17/7059
See application file for complete search history.

(56) References Cited

U.S. PATENT DOCUMENTS

| | | |
|---|---|---|
| 6,676,705 B1 | 1/2004 | Wolf |
| 6,736,851 B2 | 5/2004 | Maroney et al. |
| 6,827,740 B1 | 12/2004 | Michelson |
| 6,887,277 B2 | 6/2005 | Rauscher et al. |
| 6,942,699 B2 | 9/2005 | Stone et al. |
| 6,986,790 B2 | 1/2006 | Ball et al. |
| 7,011,686 B2 | 3/2006 | Ball et al. |
| 7,097,663 B1 | 8/2006 | Nicol et al. |
| 7,175,663 B1 | 2/2007 | Stone |
| 7,241,314 B1 | 7/2007 | Winslow |
| 7,615,080 B2 | 11/2009 | Ondrla |
| 7,753,959 B2 | 7/2010 | Berelsman et al. |
| 7,819,923 B2 | 10/2010 | Stone et al. |
| 7,918,895 B2 | 4/2011 | Isch et al. |
| 8,002,838 B2 | 8/2011 | Klotz |
| 8,052,758 B1 | 11/2011 | Winslow |
| 8,192,497 B2 | 6/2012 | Ondrla |
| 8,236,059 B2 | 8/2012 | Stone et al. |
| 8,246,687 B2 | 8/2012 | Katrana et al. |
| 8,317,871 B2 | 11/2012 | Stone et al. |
| 9,033,990 B2 | 5/2015 | Iannotti et al. |
| 10,449,054 B2 | 10/2019 | Hopkins |
| 10,849,690 B2 | 12/2020 | Hopkins |
| 10,925,658 B2 | 2/2021 | Hopkins |
| 10,925,738 B2 | 2/2021 | Winslow et al. |
| 2004/0064188 A1 | 4/2004 | Ball et al. |
| 2004/0064190 A1 | 4/2004 | Ball et al. |
| 2004/0127904 A1* | 7/2004 | Konieczynski .... A61B 17/8052 606/70 |
| 2004/0230197 A1 | 11/2004 | Tornier et al. |
| 2004/0267284 A1 | 12/2004 | Parmer et al. |
| 2005/0085915 A1* | 4/2005 | Steinberg ............... A61F 2/4014 623/23.72 |
| 2007/0112430 A1 | 5/2007 | Simmen et al. |
| 2009/0125111 A1 | 5/2009 | Copf, Jr. |
| 2009/0192621 A1 | 7/2009 | Winslow et al. |
| 2010/0016858 A1* | 1/2010 | Michel ............... A61B 17/8057 606/70 |
| 2011/0029088 A1 | 2/2011 | Rauscher et al. |
| 2011/0035013 A1 | 2/2011 | Winslow et al. |
| 2011/0106267 A1 | 5/2011 | Grant |
| 2011/0196430 A1 | 8/2011 | Walsh et al. |
| 2012/0046699 A1 | 2/2012 | Jones et al. |
| 2013/0184765 A1* | 7/2013 | Beyar ................. A61B 17/8052 606/305 |
| 2013/0261762 A1* | 10/2013 | Kennedy ............... A61F 2/3609 623/22.42 |
| 2013/0325130 A1 | 12/2013 | Viscardi et al. |
| 2014/0018862 A1* | 1/2014 | Koay .................. A61B 17/8052 606/291 |
| 2015/0150687 A1 | 6/2015 | Hopkins |
| 2018/0193150 A1 | 7/2018 | Winslow et al. |
| 2018/0303533 A1 | 10/2018 | Hopkins |
| 2018/0303551 A1 | 10/2018 | Hopkins |
| 2018/0303586 A1 | 10/2018 | Jacobsen et al. |
| 2021/0038394 A1 | 2/2021 | Winslow et al. |
| 2021/0068901 A1 | 3/2021 | Hopkins |

FOREIGN PATENT DOCUMENTS

| | | |
|---|---|---|
| CN | 102670334 A | 9/2012 |
| CN | 1596091 A | 3/2015 |
| CN | 104755047 A | 7/2015 |
| CN | 105939682 A | 9/2016 |
| CN | 110139629 A | 8/2019 |
| DE | 10123517 C1 | 11/2002 |
| DE | 102006002211 A1 | 7/2007 |
| DE | 102006002211 B4 | 9/2007 |
| EP | 0715836 A1 | 6/1996 |
| EP | 0715836 B1 | 10/2001 |
| EP | 1402854 A2 | 3/2004 |
| EP | 1402856 A1 | 3/2004 |
| FR | 2909860 A1 | 6/2008 |
| JP | 2004121849 A | 4/2004 |
| JP | 2004121850 A | 4/2004 |
| JP | 2009531085 A | 9/2009 |
| JP | 2013521095 A | 6/2013 |
| JP | 2013536022 A | 9/2013 |
| JP | 2016538929 A | 12/2016 |
| JP | 2020513930 A | 5/2020 |
| KR | 20130052542 A | 5/2013 |
| WO | WO-0182843 A2 | 11/2001 |
| WO | WO-2007109800 A2 | 9/2007 |
| WO | WO-2013165457 A1 | 11/2013 |
| WO | WO-2015084791 A1 | 6/2015 |
| WO | WO-2016053837 A1 | 4/2016 |
| WO | WO-2018129286 A1 | 7/2018 |

OTHER PUBLICATIONS

"U.S. Appl. No. 14/557,763, Final Office Action dated Jan. 23, 2017", 13 pgs.

"U.S. Appl. No. 14/557,763, Final Office Action dated Mar. 26, 2019", 11 pgs.

"U.S. Appl. No. 14/557,763, Non Final Office Action dated Jun. 27, 2017", 12 pgs.

"U.S. Appl. No. 14/557,763, Non Final Office Action dated Sep. 8, 2016", 12 pgs.

"U.S. Appl. No. 14/557,763, Non Final Office Action dated Sep. 18, 2018", 8 pgs.

"U.S. Appl. No. 14/557,763, Notice of Allowability dated Aug. 14, 2019", 2 pgs.

"U.S. Appl. No. 14/557,763, Notice of Allowance dated Jun. 10, 2019", 11 pgs.

"U.S. Appl. No. 14/557,763, Response filed Mar. 3, 2017 to Final Office Action dated Jan. 23, 2017", 12 pgs.

"U.S. Appl. No. 14/557,763, Response Filed Apr. 11, 2018 to Final Office Action dated Jan. 11, 2018", 17 pgs.

"U.S. Appl. No. 14/557,763, Response filed May 22, 2019 to Final Office Action dated Mar. 26, 2019", 18 pgs.

"U.S. Appl. No. 14/557,763, Response filed Sep. 27, 2017 to Non Final Office Action dated Jun. 27, 2017", 12 pgs.

"U.S. Appl. No. 14/557,763, Response filed Nov. 18, 2016 to Non Final Office Action dated Sep. 8, 2016", 12 pgs.

"U.S. Appl. No. 14/557,763, Response Filed Dec. 18, 2018 to Non-Final Office Action dated Sep. 18, 2018", 13 pgs.

"U.S. Appl. No. 15/863,223, Advisory Action dated Jun. 13, 2019", 3 pgs.

(56) References Cited

OTHER PUBLICATIONS

"U.S. Appl. No. 15/863,223, Final Office Action dated Mar. 19, 2019", 10 pgs.
"U.S. Appl. No. 15/863,223, Non Final Office Action dated Jul. 25, 2018", 10 pgs.
"U.S. Appl. No. 15/863,223, Response filed May 20, 2019 to Final Office Action dated Mar. 19, 2019", 13 pgs.
"U.S. Appl. No. 15/863,223, Response filed Oct. 12, 2018 to Non Final Office Action dated Jul. 25, 2018", 13 pgs.
"Australian Application Serial No. 2014357337, First Examination Report dated Aug. 3, 2018", 5 pgs.
"Australian Application Serial No. 2014357337, Response filed Jul. 17, 2019 to Subsequent Examiners Report dated Dec. 19, 2018", 13 pgs.
"Australian Application Serial No. 2014357337, Subsequent Examiners Report dated Dec. 19, 2018", 5 pgs.
"Australian Application Serial No. 2018205838, First Examination Report dated Aug. 9, 2019", 3 pgs.
"Canadian Application Serial No. 2,932,585, Office Action dated Jun. 14, 2019", 6 pgs.
"Chinese Application Serial No. 201480072332.9, Office Action dated Jan. 24, 2018", (W/ English Translation), 16 pgs.
"Chinese Application Serial No. 201480072332.9, Office Action dated Sep. 30, 2018", (W/ English Translation), 16 pgs.
"Chinese Application Serial No. 201480072332.9, Response Filed Dec. 17, 2018 to Office Action dated Sep. 30, 2018", w/English Claims, 9 pgs.
"English abstract of FR 2909860", (2008).
"European Application Serial No. 14821928.0, Communication Pursuant to Article 94(3) EPC dated Mar. 27, 2018", 5 pgs.
"European Application Serial No. 14821928.0, Response filed Oct. 8, 2018 to Communication Pursuant to Article 94(3) EPC dated Mar. 27, 2018", 12 pgs.
"European Application Serial No. 14821928.0, Response filed Dec. 16, 2016 to Communication pursuant to Rules 161(1) and 162 EPC dated Aug. 30, 2016", 12 pgs.
"European Application Serial No. 18168424.2, Extended European Search Report dated Feb. 8, 2019", 8 pgs.
"European Application Serial No. 18168597.5, Extended European Search Report dated May 14, 2019", 10 pgs.
"European Application Serial No. 18168597.5, Partial European Search Report dated Feb. 5, 2019", 10 pgs.
"International Application Serial No. PCT/US2014/068062, International Preliminary Report on Patentability dated Jun. 16, 2016", 8 pgs.
"International Application Serial No. PCT/US2014/068062, International Search Report dated Mar. 17, 2015", 4 pgs.
"International Application Serial No. PCT/US2014/068062, Written Opinion dated Mar. 17, 2015", 6 pgs.
"International Application Serial No. PCT/US2018/012537, International Preliminary Report on Patentability dated Jul. 18, 2019", 7 pgs.
"International Application Serial No. PCT/US2018/012537, International Search Report dated Apr. 10, 2018", 5 pgs.
"International Application Serial No. PCT/US2018/012537, Written Opinion dated Apr. 10, 2018", 5 pgs.
"Japanese Application Serial No. 2016-535678, Office Action dated Sep. 11, 2018", (W/ English Translation), 7 pgs.
"Japanese Application Serial No. 2016-535678, Response Filed Dec. 11, 2018 to Office Action dated Sep. 11, 2018", w/English Claims, 7 pgs.
"Practical Manual of Basic Standards for Social Public Safety Product Design", Office of Technical Supervision Committee of Ministry of Public Security, Standards Press of China, not in English, (Dec. 31, 1995), 12 pgs.
U.S. Appl. No. 14/557,763, filed Dec. 2, 2014, Adjustable Orthopedic Connections.
U.S. Appl. No. 15/863,223, filed Jan. 5, 2018, Adjustable Orthopedic Connections.
U.S. Appl. No. 15/956,494, filed Apr. 18, 2018, Guide Wire Alignment.
U.S. Appl. No. 15/956,502, filed Apr. 18, 2018, Tool for Fixed Customised Relative Alignment of Adjustable Orthopedic Devices.
"U.S. Appl. No. 15/863,223, Corrected Notice of Allowability dated Jan. 13, 2021", 2 pgs.
"U.S. Appl. No. 15/863,223, Corrected Notice of Allowability dated Dec. 4, 2020", 2 pgs.
"U.S. Appl. No. 15/863,223, Non Final Office Action dated Jan. 16, 2020", 11 pgs.
"U.S. Appl. No. 15/863,223, Notice of Allowance dated Jul. 28, 2020", 5 pgs.
"U.S. Appl. No. 15/863,223, Response filed Apr. 13, 2020 to Non Final Office Action dated Jan. 16, 2020", 13 pgs.
"U.S. Appl. No. 15/956,494, Final Office Action dated Aug. 4, 2020", 7 pgs.
"U.S. Appl. No. 15/956,494, Non Final Office Action dated Mar. 17, 2020", 6 pgs.
"U.S. Appl. No. 15/956,494, Notice of Allowance dated Oct. 22, 2020", 7 pgs.
"U.S. Appl. No. 15/956,494, Response filed Jun. 17, 2020 to Non Final Office Action dated Mar. 17, 2020", 15 pgs.
"U.S. Appl. No. 15/956,494, Response filed Oct. 2, 2020 to Final Office Action dated Aug. 4, 2020", 10 pgs.
"U.S. Appl. No. 15/956,494, Response Filed Dec. 3, 2019 to Restriction Requirement Filed Oct. 3, 2019", 7 pgs.
"U.S. Appl. No. 15/956,502, Non Final Office Action dated Jan. 10, 2020", 8 pgs.
"U.S. Appl. No. 15/956,502, Notice of Allowance dated Jul. 28, 2020", 9 pgs.
"U.S. Appl. No. 15/956,502, Response filed Apr. 1, 2020 to Non Final Office Action dated Jan. 10, 2020", 12 pgs.
"U.S. Appl. No. 15/956,502, Response filed Dec. 13, 2019 to Restriction Requirement dated Oct. 24, 2019", 7 pgs.
"U.S. Appl. No. 15/956,502, Restriction Requirement dated Oct. 24, 2019", 7 pgs.
"U.S. Appl. No. 17/082,812, Preliminary Amendment filed Jan. 18, 2021", 6 pgs.
"Canadian Application Serial No. 2,932,585, Office Action dated Apr. 7, 2020", 3 pgs.
"Canadian Application Serial No. 2,932,585, Response filed May 12, 2020 to Office Action dated Apr. 7, 2020", 4 pgs.
"Canadian Application Serial No. 2,932,585, Response filed Dec. 16, 2019 to Office Action dated Jun. 14, 2019", 16 pgs.
"Canadian Application Serial No. 3,049,585, Office Action dated Sep. 1, 2020", 3 pgs.
"Canadian Application Serial No. 3,049,585, Response filed Dec. 22, 2020 to Office Action dated Sep. 1, 2020", 22 pgs.
"Chinese Application Serial No. 201880005681.7, Office Action dated Mar. 29, 2021", (W/ English Translation), 5 pgs.
"Chinese Application Serial No. 201880005681.7, Office Action dated Sep. 27, 2020", with English translation, 13 pages.
"Chinese Application Serial No. 201880005681.7, Response filed Dec. 9, 2020 to Office Action dated Sep. 27, 2020", w/ English claims, 11 pgs.
"European Application Reference No. 18701851.0, Response to Communication pursuant to Rules 161(1) and 162 EPC filed Mar. 2, 2020", 12 pgs.
"European Application Serial No. 14821928.0, Communication Pursuant to Article 94(3) EPC dated Feb. 20, 2020", 4 pgs.
"European Application Serial No. 14821928.0, Communication Pursuant to Article 94(3) EPC dated Sep. 13, 2021", 4 pgs.
"European Application Serial No. 14821928.0, Response filed Jul. 1, 2020 to Communication Pursuant to Article 94(3) EPC dated Feb. 20, 2020", 28 pgs.
"European Application Serial No. 18168597.5, Response filed Dec. 12, 2019 to Extended European Search Report dated May 14, 2019", 16 pgs.
"European Application Serial No. 18701851.0, Communication Pursuant to Article 94(3) EPC dated Apr. 22, 2021", 3 pgs.
"European Application Serial No. 18701851.0, Communication Pursuant to Article 94(3) EPC dated Sep. 10, 2020", 5 pgs.

(56) References Cited

OTHER PUBLICATIONS

"European Application Serial No. 18701851.0, Response filed Jan. 20, 2021 to Communication Pursuant to Article 94(3) EPC dated Sep. 10, 2020", 15 pgs.

"European Application Serial No. 18701851.0, Response filed Aug. 31, 2021 to Communication Pursuant to Article 94(3) EPC dated Apr. 22, 2021", 66 pgs.

"Japanese Application Serial No. 2019-537181, Notification of Reasons for Refusal dated Aug. 10, 2021", w/ English Translation, 5 pgs.

"Japanese Application Serial No. 2019-537181, Notification of Reasons for Refusal dated Nov. 10, 2020", w/ English Translation, 8 pgs.

"Japanese Application Serial No. 2019-537181, Response filed Feb. 9, 2021 to Notification of Reasons for Refusal dated Nov. 10, 2020", w/ English claims, 15 pgs.

"Japanese Application Serial No. 2019-537181, Response filed Nov. 10, 2021 to Notification of Reasons for Refusal dated Aug. 10, 2021", w/ English Translation, 10 pgs.

"Korean Application Serial No. 10-20165-7017889, Notice of Preliminary Rejection dated Dec. 19, 2019", (W/ English Translation), 10 pgs.

"Korean Application Serial No. 10-20165-7017889, Response filed Feb. 26, 2020 Notice of Preliminary Rejection dated Dec. 19, 2019", (W/ English Translation of Claims), 8 pgs.

U.S. Appl. No. 17/082,773, filed Oct. 28, 2020, Adjustable Orthopedic Conections.

U.S. Appl. No. 17/082,812, filed Oct. 28, 2020, Tool for Fixed Customised Relative Alignment of Adjustable Orthopedic Devices.

"U.S. Appl. No. 14/557,763, Notice of Allowability dated Sep. 11, 2019", 3 pgs.

"U.S. Appl. No. 15/956,494, Restriction Requirement dated Oct. 3, 2019", 8 pgs.

"Australian Application Serial No. 2018205838, Response filed Oct. 9, 2019 First Examination Report dated Aug. 9, 2019", 22 pgs.

"European Application Serial No. 18168424.2, Response filed Sep. 13, 2019 to Extended European Search Report dated Feb. 8, 2019", 16 pgs.

"European Application Serial No. 14821928.0, Response filed Jan. 24, 2022 to Communication Pursuant to Article 94(3) EPC dated Sep. 13, 2021", 16 pgs.

"U.S. Appl. No. 17/082,812, Restriction Requirement dated Jul. 7, 2022", 5 pgs.

"U.S. Appl. No. 17/082,812, Response filed Jul. 18, 2022 to Restriction Requirement dated Jul. 7, 2022", 7 pgs.

"U.S. Appl. No. 17/082,773, Preliminary Amendment filed Sep. 27, 2022", 6 pgs.

"U.S. Appl. No. 17/082,812, Non Final Office Action dated Oct. 26, 2022", 10 pgs.

"U.S. Appl. No. 17/082,812, Notice of Allowance dated Apr. 5, 2023", 8 pgs.

"U.S. Appl. No. 17/082,812, Response filed Jan. 20, 2023 to Non Final Office Action dated Oct. 26, 2022", 13 pgs.

\* cited by examiner

ADJUSTABLE ORTHOPEDIC CONNECTIONS

CLAIM OF PRIORITY

This application is a divisional of U.S. patent application Ser. No. 14/557,763, filed on Dec. 2, 2014, now issued as U.S. Pat. No. 10,449,054, which claims the benefit of U.S. Provisional Patent Application Ser. No. 61/910,700, filed on Dec. 2, 2013, the benefit of priority of each of which is claimed hereby, and each of which is incorporated by reference herein in its entirety.

TECHNICAL FIELD

The present disclosure relates generally to medical technology and in certain aspects to methods and systems for adjustably connecting orthopedic components, e.g., an articulating member to a stem or base.

BACKGROUND

As further background, the head or other portions of a proximal humerus can be replaced with prosthetic devices, e.g., to treat advanced degeneration of the proximal humerus. Due to the variability of the anatomy, e.g., head height, diameter, inclination and offset to the humeral canal, effective anatomical reconstruction can often necessitate a modular system offering a variety of implant configurations.

OVERVIEW

The present disclosure provides, in certain aspects, unique methods and systems for integrating or connecting orthopedic components. Illustratively, one aspect of the present disclosure provides a connecting assembly for connecting a plurality of orthopedic components. This particular connecting assembly includes a first orthopedic component that provides a bore. The assembly also includes a second orthopedic component that can be or include a quasi-spherical member that is positionable in the bore of the first orthopedic component for removeably locking the quasi-spherical member to the first orthopedic component. The quasi-spherical member includes a textured outer surface such as any of those disclosed herein. The textured outer surface can contact walls of the bore in a manner that removeably locks or helps to removeably lock the quasi-spherical member to the first orthopedic component. While not necessary, any suitable combination of the following features can be incorporated into or associated with the connecting assembly. The quasi-spherical member can be part of a bone screw or fastener. Such a bone screw can include a shaft (e.g., a fully or partially threaded shaft with or without one or more tapered and/or one or more non-tapered longitudinal sections) that extends away from the quasi-spherical member, for example, where the quasi-spherical member forms all or part of a head of the screw. The orthopedic component can be an implant. The orthopedic component can be a bone plate. With a bone plate, the bore can extend partially or entirely through a wall of the plate. In some forms, a bore will extend entirely through a wall of the plate and a leading tip of the screw will be passed through the bore in advance of the quasi-spherical member. The first orthopedic component can be an articulating ball or head member such as a humeral head. The quasi-spherical member can be a modular component that is connectable to a separate humeral stem component. The textured surface can cover a significant portion of the quasi-spherical member such as more than 25% or more than 50%. The textured outer surface can include a plurality of planar surface elements, e.g., with polygonal perimeters.

In one aspect, the present disclosure provides a ball-side prosthesis for articulating with a socket in a ball and socket joint in a patient. This particular prosthesis comprises an articulating ball member that includes a top side and a bottom side. The top side provides a convex articulating surface for articulating with surfaces in the socket. The bottom side includes an opening into a bore that extends into the articulating ball member from the bottom side toward the top side. The prosthesis further comprises a fixation member that is anchorable to a bone of the patient remaining on the ball side of the ball and socket joint. The prosthesis further comprises a quasi-spherical member that is disposed at a proximal end of the fixation member. The quasi-spherical member is positionable in the bore of the articulating ball member for removeably locking the quasi-spherical member to the articulating ball member. The quasi-spherical member includes a textured outer surface such as any of those disclosed herein for contacting walls of the bore. While not necessary, any suitable combination of the following features can be incorporated into or associated with the prosthesis. The fixation member can include an elongate stem that is receivable in an intramedullary canal on the ball side of the ball and socket joint. The articulating ball member can be a humeral head. The bore can include a tapered segment. The fixation member and the quasi-spherical member can be modular components that are connectable to one another, e.g., using a Morse-type taper connection. The textured outer surface can cover any suitable percentage of the quasi-spherical member, e.g., between about 10% and 100%, or between about 40% and about 99%, or between about 50% and about 90%. The textured outer surface can include a plurality of generally planar faces, e.g., including generally planar faces spaced from one another on the quasi-spherical member and/or including generally planar faces contiguous with one another on the quasi-spherical member. The textured outer surface can include a plurality of surface elements with polygonal perimeters, e.g., including surface elements with planar surfaces within the polygonal perimeters and/or including surface elements with convex and/or concave surfaces within the polygonal perimeters. The textured outer surface can include a three-dimensional tessellation incorporating polygonal surfaces. The quasi-spherical member can approximate a honeycomb of polyhedral cells.

In one aspect, the present disclosure provides a quasi-spherical member that is positionable in the bore of an orthopedic component for removeably locking the quasi-spherical member to the orthopedic component. The quasi-spherical member comprises a textured outer surface that includes a plurality of outermost extensions that are spaced from one another on the textured outer surface and which define a first radius of the quasi-spherical member and a plurality of innermost depressions that are spaced from one another on the textured outer surface and which define a second radius of the quasi-spherical member. The textured outer surface can contact walls of the bore in a manner that removeably locks or helps to removeably lock the quasi-spherical member to the orthopedic component. While not necessary, any suitable combination of the following features can be incorporated into or associated with the quasi-spherical member or orthopedic component. The bore can include a tapered segment with a first diameter that is twice the first radius and a second diameter that is twice the second radius. The plurality of innermost depressions can occur on planar and/or non-planar (e.g., concave) surfaces on the quasi-spherical member. The plurality of outermost extensions can be symmetrical peaks on the quasi-spherical member.

In one aspect, the present disclosure provides a humeral prosthesis for articulating with a glenoid cavity in a patient. This particular humeral prosthesis comprises a humeral head member that includes a top side and a bottom side. The top side provides a convex articulating surface for articulating with surfaces in the glenoid cavity, e.g., a native glenoid cavity. The bottom side includes an opening into a bore that extends into the humeral head member from the bottom side toward the top side. The prosthesis further includes a fixation member that is anchorable to a humerus of the patient. The prosthesis further includes a quasi-spherical member that is disposed at a proximal end of the fixation member, e.g., where the quasi-spherical member is an integral part of the fixation member. The quasi-spherical member is positionable in the bore of the humeral head member for removeably locking the quasi-spherical member to the humeral head member. The quasi-spherical member includes a textured outer surface such as any of those disclosed herein for contacting walls of the bore. In one embodiment, the textured outer surface includes a plurality of outermost extensions that are spaced from one another on the textured outer surface and which define a first radius of the quasi-spherical member and a plurality of innermost depressions that are spaced from one another on the textured outer surface and which define a second radius of the quasi-spherical member. While not necessary, the fixation member can include an elongate stem that is receivable in an intramedullary canal on the ball side of the ball and socket joint and/or the textured outer surface can include a three-dimensional tessellation of triangular surfaces whose vertices provide the plurality of outermost extensions.

In some aspects, the present disclosure provides systems and methods that can be used in a humeral reconstruction surgery in which the head or proximal end of the humerus bone is replaced or repaired, e.g., providing surgeons with modular humeral head systems offering rapid and accurate adjustability. In some forms, modular humeral heads will have eccentric centers and/or be used with stemmed or stemless humeral fixation members.

Some aspects of the present disclosure involve connections between a female-type bore in a first orthopedic member such as an orthopedic plate (e.g., a bone plate) and a quasi-spherical member or other male-type connector of a second orthopedic member. This second member can be any orthopedic element or device to be connected to the plate. In certain embodiments, this second member will be something to be driven into or otherwise received in bone, for example, to attach the plate to a bone. This second member can be a screw, fastener, pin, spike, or nail. For example, the second member can be a screw with a tapered shaft, or having a significant longitudinal section of the shaft being tapered with or with threading. In some embodiments, the first orthopedic member will be a non-plate orthopedic device. In some embodiments, the first orthopedic member will be an orthopedic implant (e.g., a knee, hip, shoulder, ankle, or other joint implant). Each of these non-limiting examples can stand on its own, or can be combined in various permutations or combinations with one or more of the other examples.

BRIEF DESCRIPTION OF THE DRAWINGS

Corresponding reference characters indicate corresponding parts throughout the several views. The exemplifications set out herein illustrate exemplary embodiments of the invention, and such exemplifications are not to be construed as limiting the scope of the invention in any manner. In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1B:
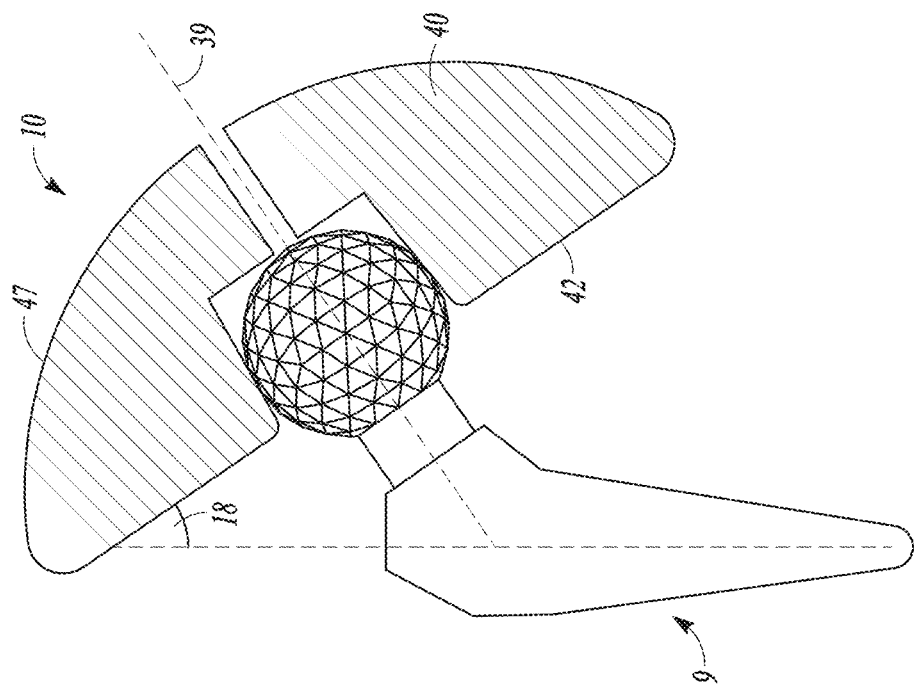
FIG. 1B shows an alternative orientation of the humeral prosthesis of FIG. 1A.

As disclosed above, the present disclosure provides, in certain aspects, unique methods and systems for making orthopedic connections. Illustratively, some embodiments of the present disclosure provide a connecting assembly for connecting a plurality of orthopedic components, e.g., where the connecting assembly itself provides a unique way to spatially adjust a first component relative to a second component. Such connecting assemblies can include a first orthopedic component that provides a female bore. Additionally the assembly can include a second orthopedic component that can be or include a male-type connecting member that is positionable in the bore of the first orthopedic component. In one preferred form, the male-type connecting member will include a quasi-spherical member. The quasi-spherical member includes a textured outer surface, e.g., for contacting one or more walls or surfaces in the bore in a fashion that removeably locks or helps to removeably lock or fix the quasi-spherical member in the bore. Other suitable male-type connecting members incorporating textured outer surfaces in accordance with the present disclosure can approximate other shapes (e.g., non-spherical shapes such as a quasi-ellipsoid shape) as discussed elsewhere herein. In some preferred embodiments, the geometry of the textured outer surface will allow the quasi-spherical member to be positioned and locked in the bore in a rather large number of orientations or angular positions, for example, to account for variability in the patient's anatomy. In some instances, such a connecting assembly will be part of a ball-side prosthesis for articulating with a socket in a ball and socket joint in a patient. For example, the first orthopedic component can be an articulating ball member such as a humeral head member that includes a top side and a bottom side. The top side can provide a convex articulating surface for articulating with surfaces in the socket. The bottom side can include an opening into the bore, e.g., extending into the articulating ball member from the bottom side toward the top side. The quasi-spherical member can be disposed at the proximal end of a fixation member that is anchorable to a bone of the patient remaining on the ball side of the ball and socket joint. In the context of a humeral prosthesis, for example, the orientation or angular position of the quasi-spherical member in the bore can be adjusted to account for variability in things like head height, diameter, inclination and offset to the humeral canal. In some embodiments, the first orthopedic component is a bone plate, and the second orthopedic component is a bone screw such as where a leading tip of a shaft of the screw is passed through the plate through the female bore and into the bore in advance of a quasi-spherical member that forms part of the screw, e.g., forming all or part of a head of the screw. Thereafter, the quasi-spherical member can be received and locked in the bore in a rather large number of orientations or angular positions for attaching the plate to bone, for example, by advancing the screw to a desired final location in the bone. Such connections can be effective to resist back-out of the screw, in some instances, a shaft or a leading tip of a shaft never passes through a female bore in a plate. In some embodiments, a leading tip of the shaft enters bone before the screw contacts or is associated with the plate. In some forms, a screw is advanced to a desired final location in the bone before the quasi-spherical member is locked in the female bore, for example, where a plate is impacted down onto a pre-positioned screw so that the quasi-spherical member is forcefully received and locked in the female bore.

Figure 1A:
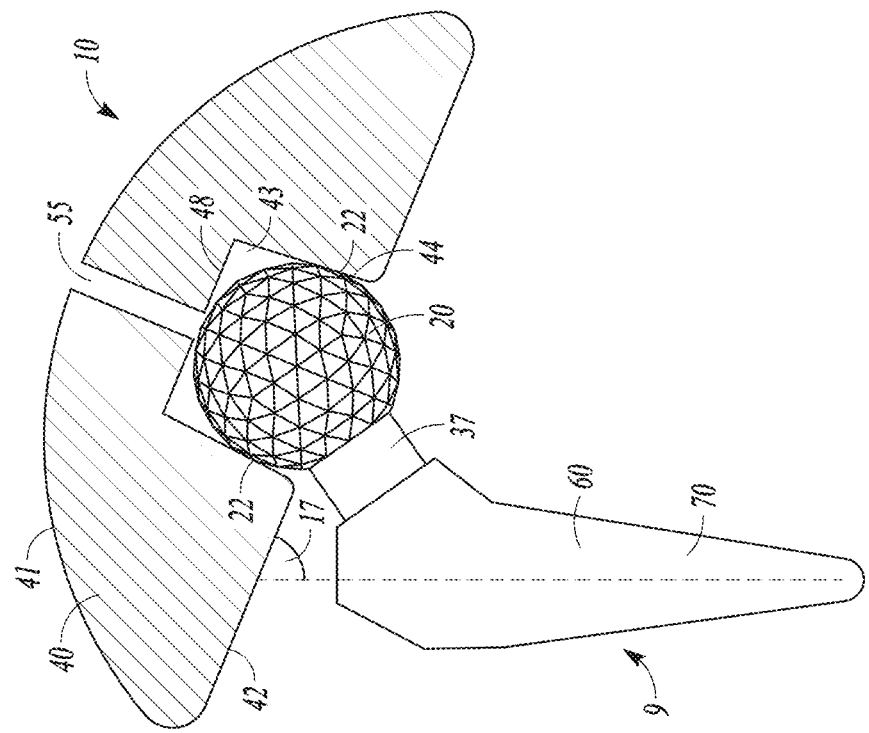
FIG. 1A shows a humeral prosthesis according to one embodiment of the present disclosure.
Figure 1C:
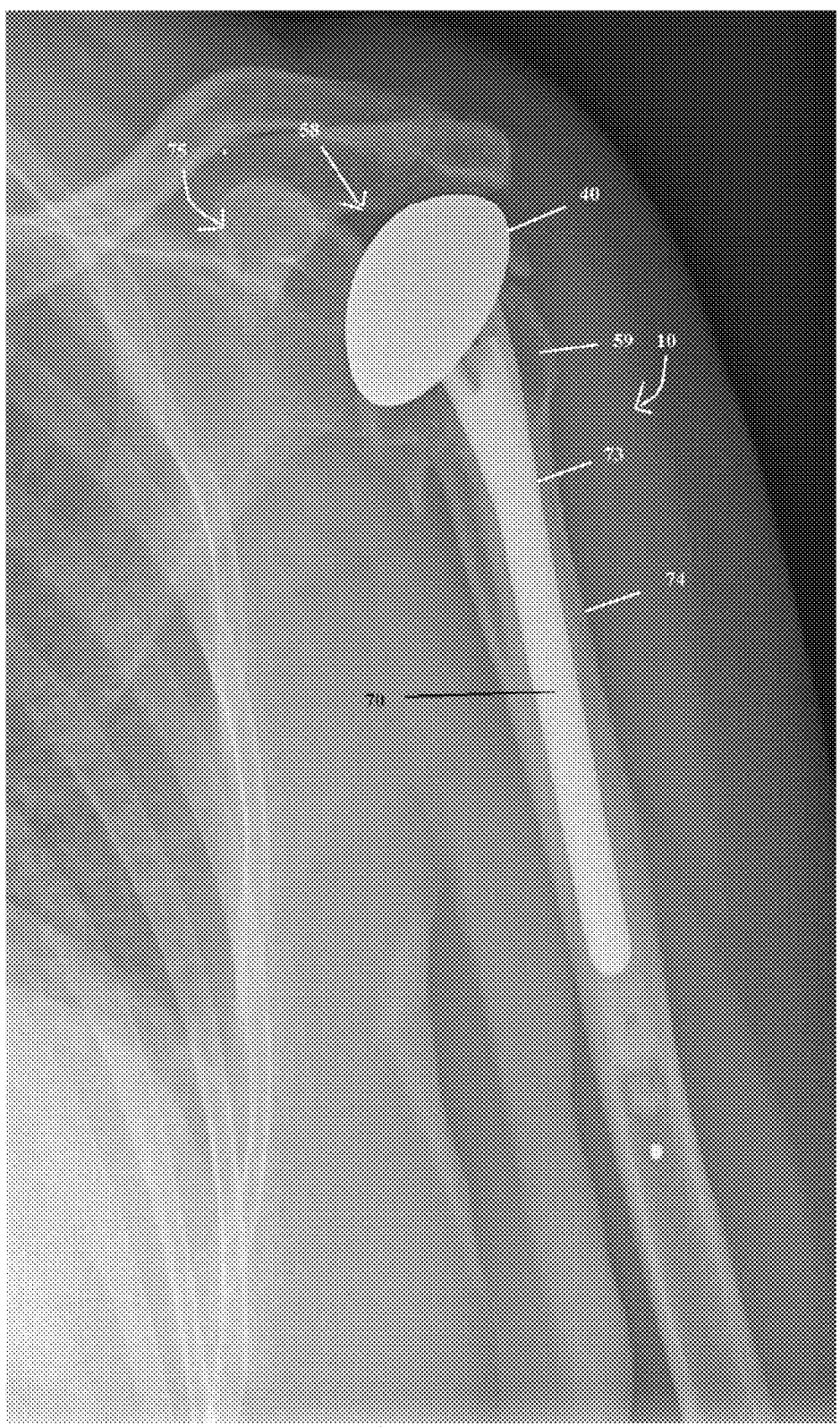
FIG. 1C shows a radiographic image of an illustrative humeral prosthesis.

FIGS. 1A-1B show an illustrative humeral prosthesis 10. This particular humeral prosthesis 10 includes a humeral head member 40, a quasi-spherical member 20, and a humeral fixation member 60. The humeral head member 40 includes a top side 41 and a bottom side 42. The humeral head member 40 can be hemispherical or partially-spherical in shape and in this particular instance the top side 41 provides a convex articulating surface 47 for articulating with glenoid surfaces, e.g., natural or synthetic mating glenoid surfaces of a human or animal shoulder. The humeral head member 40 can be formed with any suitable material including metals, ceramics, polymers or combinations of these materials. The humeral fixation member 60 is anchorable to a humerus. The humeral fixation member 60 includes a stem 70 which is sized and shaped to be inserted into a canal 73 of the humerus 74 (See FIG. 1C). The stem 70 can be anchored in any suitable manner such as being cemented, non-cemented, pinned, or screwed to the surrounding bone material and can be configured to promote bone ingrowth. The stem 70 can be formed with any suitable material including metals, ceramics, polymers or combinations of these materials. FIG. 1C is a radiographic image of a humeral prosthesis implanted after an illustrative shoulder replacement surgery. The stem 70 of the fixation member 60 can be installed in the canal 73 of a humerus bone 74. The humeral head member (head) 40 can be located at the proximal end 59 of the humerus 74 and can articulate with natural or synthetic mating glenoid surfaces 58 of the shoulder 75.

Referring to FIGS. 1A-1B, during a shoulder replacement in which a humeral prosthesis 10 is required and perhaps owing to variations in anatomy, a surgeon may elect to adjust the orientation or angular position of a humeral head 40 (shown in cross section) relative to a remaining anatomical structure or another implant component such as humeral fixation member 60. The humeral head member 40 includes a bottom side 42 that provides a bore 43 with one or more smooth walls 44. The bore extends into the humeral head member from the bottom side toward the top side. The bore 43 can be tapered with the opening wider at the bottom side 42 and narrowing towards a base 48 forming a bottom of the bore 43. A suitable female bore can be tapered or non-tapered. A suitable female-type bore can be or incorporate any suitable three-dimensional shape, e.g., incorporating rectilinear and/or curvilinear features. A suitable female-type bore can have a frustoconical shape. Suitable shapes of a female-type bore can be or include full and partial forms of wedges, tapered bodies, toroids, conoids, catenoids, cubes, parallelepipeds, prisms, and combinations of the same. Suitable shapes include but are not limited to full or partial cylinders, cuboids, cones, pyramids, and tetrahedrons, and combinations of the same, and in this regard, it will be understood that male-type connectors incorporating textured outer surfaces in accordance with certain aspects of the present disclosure can approximate any suitable shape as well. Thus, in addition to spheres, such male-type connecting members can approximate non-spherical shapes, e.g., incorporating any suitable three-dimensional rectilinear and/or curvilinear shape. Illustratively, in some preferred forms, a male-type connector incorporating a textured outer surface in accordance with the present disclosure will approximate all or part of a shape like a sphere (e.g., a partial sphere such as a hemisphere), ellipsoid, oblate spheroid, prolate spheroid, catenoid, conoid, or paraboloid of revolution.

Continuing with FIGS. 1A-B, contact between the quasi-spherical member 20 and walls 44 of the bore at one or more interfaces 22 can allow a surgeon to orient the humeral head 40 in a wide range of positions, two of which can be seen in the different angles of the humeral head 40 illustrated in FIGS. 1A and 1B. FIG. 1A shows the relationship between the fixation member 60 and the humeral head 40 at a first angle 17 and FIG. 1B shows the relationship between the fixation member 60 and the humeral head 40 at a second angle 18. The geometry of the quasi-spherical member 20 can allow these angular adjustments to be made in three dimensions. During an evaluation of the orientation or angular position of the humeral head 40, the quasi-spherical member 20 may be only partially inserted into the bore 43. Even then, there may be sufficient grip to hold the components together to allow the surgeon to judge the suitability of the positioning. Once the humeral head 40 is deemed by a surgeon to be suitably oriented, the quasi-spherical member 20 can then be more fully inserted into the bore 43, e.g., by impaction loading accomplished by pressure, impact force or otherwise. In some instances, forcible contact between a male-type member such as quasi-spherical member 20 and walls of the bore will be sufficient to crush or to otherwise deform surface features of the male-type member and/or surfaces or walls within the female bore. The shape of the bore 43 including its walls 44 and the shape and surface features of the quasi-spherical member 20 can be such that the quasi-spherical member can be positionable in the bore of the humeral head member for removeably locking the quasi-spherical member to the humeral head member, e.g., providing a fixed immovable connection between the quasi-spherical member 20 and the humeral head 40.

The quasi-spherical member 20 is disposed at a proximal end of the fixation member 60. In this particular embodiment, the humeral prosthesis 10 can include a narrowing and connecting member 37 which can form a transition between the quasi-spherical member 20 and the fixation member 60. This connecting member 37 can be sized and shaped to provide clearance for adjustment of the humeral head 40 on the quasi-spherical member 20. The humeral head 40 can include a cannulation 55 providing an opening extending from the base 48 of the bore 43 to the articulating surface 47. The cannulation 55 can be used for insertion of a pin-like tool (not pictured) to separate the humeral head 40 from the quasi-spherical member 20 after the two members have been fixedly attached by impact loading. In another example, the cannulation 55 can be threaded to use in conjunction with a bolt (not pictured) to separate the humeral head member 40 from the quasi-spherical member 20. Although the bore 43 is illustrated as positioned on a center axis 39 of the humeral head 40, the placement of the bore 43 can be offset from the center axis 39 to provide a surgeon with additional configurations for the humeral prosthesis 10.

Figure 2:
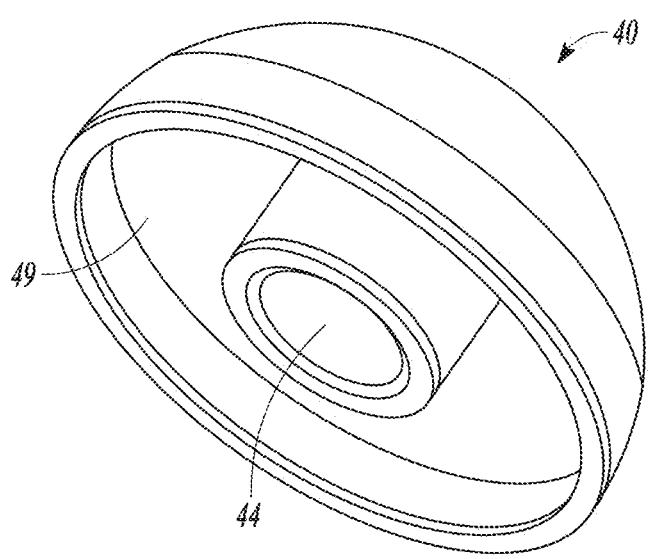
FIG. 2 shows a humeral head member according to one embodiment of the present disclosure.

FIG. 2 shows a perspective view of another example of a humeral head member 40. The bottom side 42 can include a recessed area 49 which can provide a humeral head member 40 with a lighter weight and/or greater orientation adjustment.

Figure 3A:
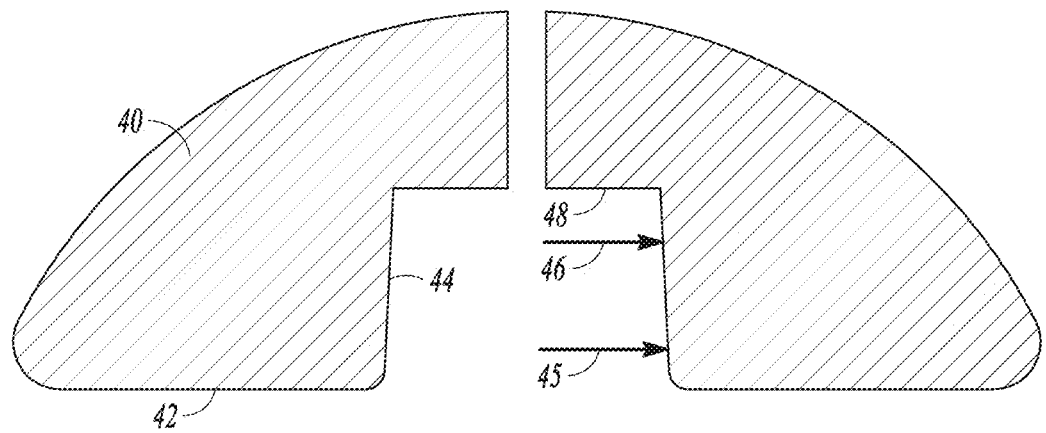
FIG. 3A shows a side, cross-sectional view of a humeral head member according to one embodiment of the present disclosure.
Figure 3B:
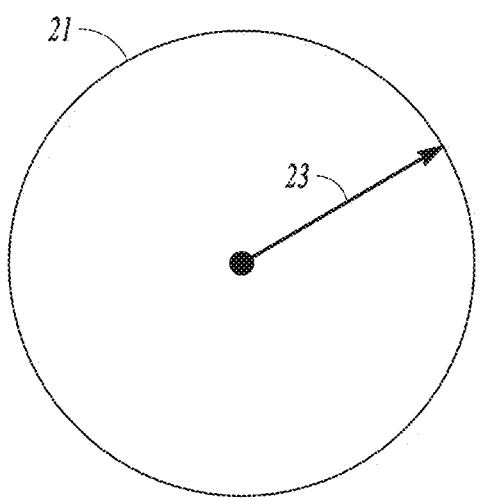
FIG. 3B illustrates a radius of a perfect sphere.
Figure 3C:
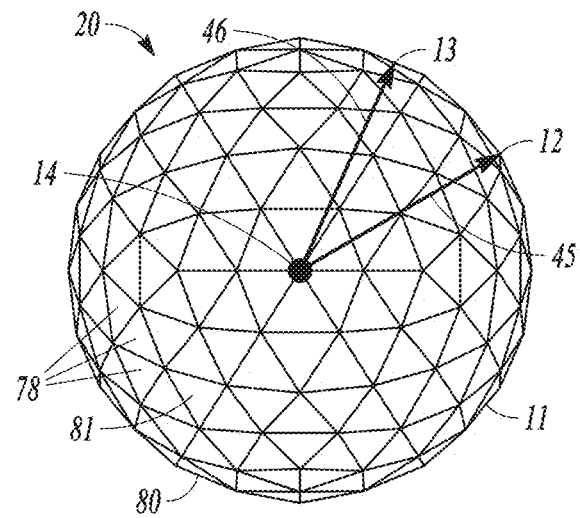
FIG. 3C shows a quasi-spherical member with a textured outer surface according to one embodiment of the present disclosure.

FIG. 3A shows a cross section of a humeral head 40. The bore 43 can be tapered so as to include a first radius 45 positioned near the bottom side 42 and a second radius 46 positioned near the base 48. While not necessary, the first radius 45 and the second radius 46 can be related to measurements on the quasi-spherical member 20 (See FIG. 3C). FIG. 3B illustrates a perfect sphere 21 having a radius 23. FIG. 3C illustrates a quasi-spherical member 20 that includes an illustrative textured outer surface 11 covering essentially the entirety of the quasi-spherical member 20. In accordance with certain aspects of the present disclosure, quasi-spherical members or other male-type connectors in accordance with the present disclosure will incorporate a textured outer surface covering more than 50%, or more than 65%, or more than 75%, or more than 85% of the quasi-spherical member or other connector. In some instances, the textured outer surface will cover between about 25% and about 50% of the quasi-spherical member or other connector, or between about 35% and about 75%, or between about 50% and about 90%, or between about 60% and about 100%.

Continuing with FIG. 3C, this particular textured outer surface 11 incorporates a three-dimensional tessellation 80. A suitable tessellation can incorporate a plurality of polygonal elements such as polygonal elements 78. In this particular instance, the polygonal elements are triangular elements or faces 81. Textured outer surfaces according to additional aspects of the present disclosure can incorporate other suitable three-dimensional tessellations. In certain embodiments, quasi-spherical members or other male-type connectors in accordance with the present disclosure will mimic or approximate a plurality of stacked polyhedra such as but not limited to stacked cubes, rhombic dodecahedrons, truncated octahedrons, hexagonal prisms, or triangular prisms. In some forms, quasi-spherical members or other male-type connectors in accordance with the present disclosure will mimic or approximate a honeycomb of polyhedral cells including uniform and non-uniform honeycombs.

Continuing with FIG. 3C, the textured outer surface 11 includes a plurality of outermost extensions 12 which in this illustrative embodiment occur at vertices of the triangular faces as discussed herein below. A distance from the center of the quasi-spherical member 20 to an outermost extension 12 can be equal to the first radius 45. While not necessary, an arc connecting at least two of the outermost extension 12 can have generally the same curvature as the arc of the perfect sphere 21. The textured outer surface 11 includes a plurality of innermost depressions 13 which in this illustrative embodiment occur at the centers of the triangular faces as discussed herein below. A distance from the center of the quasi-spherical member 20 to an innermost depression 13 can be equal to the second radius 46. While not necessary, an arc connecting at least two of the innermost depressions can have generally the same curvature as the arc of the perfect sphere 21. A secure grip between the textured outer surface 11 and inner walls 43 of the bore can occur at one or more interfaces 22. While not necessary, the relationship between the first radius 45 and the second radius 46 can be as follows: where R=a radius 23 of a perfect sphere 21, the first radius 45=R+t and the second radius 46=R−t where "t" is a variable that can be changed to create variable textured surfaces 11.

Figure 4A:
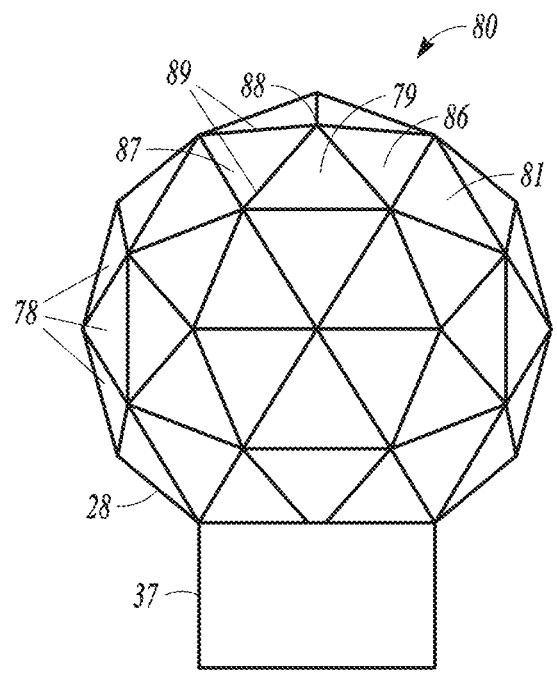
FIGS. 4A-4D show quasi-spherical members with textured outer surfaces of different densities according to additional embodiments of the present disclosure.
Figure 4B:
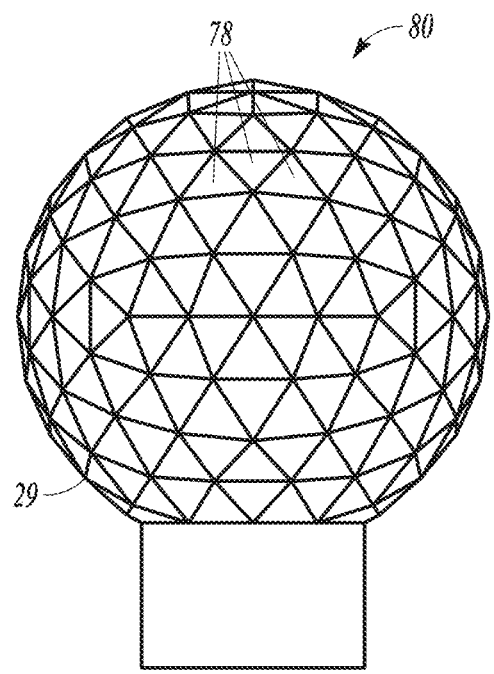
Figure 4C:
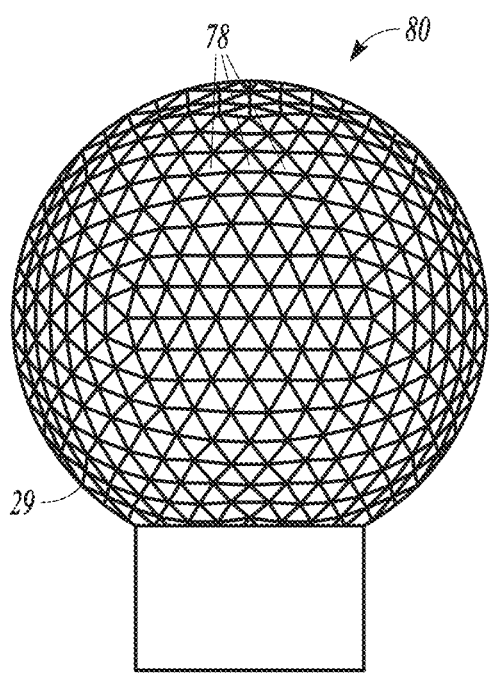
Figure 4D:
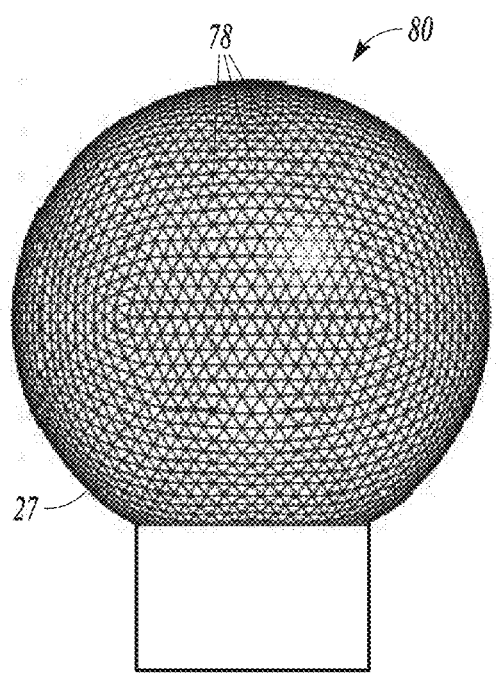

FIGS. 4A-D illustrate a spectrum of densities of tessellation patterns 80. FIG. 4A provides a quasi-spherical member 20 with a low density 28 of polygonal elements 78. FIG. 4D provides a quasi-spherical member 20 with a high density 27 of polygonal elements 78. FIGS. 4B-4C illustrate quasi-spherical members 20 with lower and higher intermediate densities 29 of polygonal elements 78. A quasi-spherical member 20 with a higher density will allow a higher quality of spherical mapping. As the quasi-spherical member 20 is being adjusted in the taper 44 (see FIGS. 1A-B), higher quality mapping can allow a greater spectrum of possible orientations or angular positions of the humeral head member 40 in relation to the quasi-spherical member 20.

FIG. 4A shows features of the polygonal surface elements 78. An individual polygon 86 can have an exterior face 87 that forms an outer surface on the quasi-spherical member 20. The exterior face 87 can include a chord 89 as an edge of the exterior face 87. Each cord 89 can be contiguous with a chord 89 of a neighboring polygon 79. The chord 89 can terminate at each end in a vertex 88. Each vertex 88 of a polygon 86 can be contiguous with a vertex 88 of a neighboring polygon 79. Any number of these exterior surface features (e.g., edges, chords, planar or non-planar faces, vertices, etc.) and/or any of the other exterior surface features disclosed herein that can be incorporated into a textured outer surface of a male-type connecting members can forcibly contact walls or surfaces in a female-type bore to some degree, and in some instances, can be formed with materials that cause such surface features to be crushed or to otherwise deform upon such forcible contact, to removeably lock or help to removeably lock the male-type connecting member in the bore. Just to give one illustrative example, a plurality of planar or nearly planar faces on a textured outer surface of a male-type connecting member (e.g., a quasi-spherical member) can each partially contact a curved wall of a female bore (e.g., cylindrical or conical).

In accordance with certain aspects of the present disclosure, quasi-spherical members or other male-type connectors in accordance with the present disclosure will incorporate a textured outer surface that includes a plurality of generally planar surfaces, for example, where the combined area of the generally planar surfaces cover more than 50%, or more than 65%, or more than 75%, or more than 85% of the quasi-spherical member or other male-type connecting member. In some instances, the combined area of the generally planar surfaces will cover between about 25% and about 50% of the quasi-spherical member or other male-type connecting member, or between about 35% and about 75%, or between about 50% and about 90%, or between about 60% and about 100%.

Figure 5A:
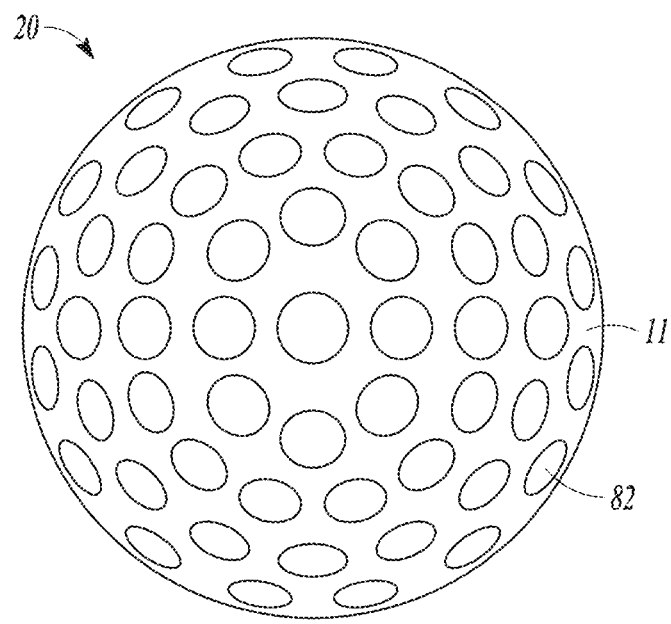
FIG. 5A shows a quasi-spherical member with a textured outer surface according to one embodiment of the present disclosure.
Figure 5B:
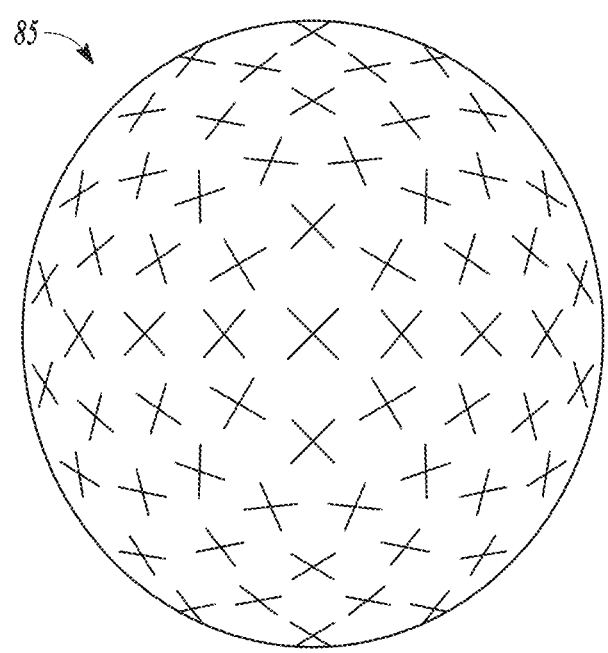
FIG. 5B shows a quasi-ellipsoid member with a textured outer surface according to one embodiment of the present disclosure.

Referring now to FIG. 5A, shown is a quasi-spherical member 20 according to another embodiment of the present disclosure that could be incorporated into any suitable orthopedic system or implant. On what would otherwise be a perfect sphere, a textured outer surface 11 in this instance includes a plurality of planar, circular faces 82 which are spaced from one another on the quasi-spherical member. These types of planar faces can have any suitable perimeter shape, e.g., incorporating rectilinear and/or curvilinear features. Illustratively, in additional embodiments, a textured outer surface will include a plurality of planar surfaces that are non-circular, e.g., polygonal. One example of this is the tessellated surface pattern shown in FIG. 3C. Additionally, it will be understood that when a textured outer surface in accordance with the present disclosure incorporates circular and/or non-circular exterior faces, such faces need not be planar. Illustratively, in additional embodiments, a textured outer surface will include a plurality of non-planar surface elements that are spaced from one another on the quasi-spherical member or other male-type connecting member. Such surface elements can be convex or concave or can incorporate other three-dimensionally curved surfaces. For example, one or more of the planar, circular faces 82 shown in FIG. 5A could instead be slightly convex or slightly concave. Additionally, it will be understood that any two such circular or non-circular surface elements need not be spaced from one another on a textured outer surface of a male-type connecting member. Select surface elements can be contiguous with one another or otherwise contact one another on the textured outer surface. FIG. 5B shows a quasi-ellipsoid member 85 according to one embodiment of the present disclosure that could be incorporated into any suitable orthopedic system or implant. A textured outer surface 11 in this instance includes a plurality of surface elements "X" which can be any of those disclosed herein, e.g., planar and/or non-planar surface elements. For example, any one surface element "X" can be a bump, bulge, lump, knob, protuberance, dimple, depression, dent, or other type of projection or indentation. Such features can be arranged in regular or irregular patterns. These and other surface textures disclosed herein can be formed in any suitable manner including by cutting away, grinding away or otherwise removing material from an initial work piece to provide one or more surface features or elements, or by welding, adhering or otherwise adding material to an existing piece to provide one or more surface features or elements, or by casting or otherwise initially forming a component (e.g., using an additive manufacturing process) to have one or more surface features or elements.

Figure 6A:
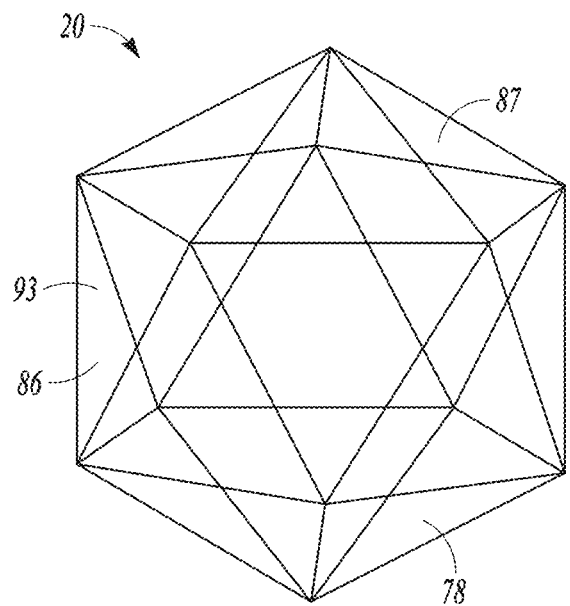
FIG. 6A shows a quasi-spherical member with a textured outer surface according to one embodiment of the present disclosure.
Figure 6B:
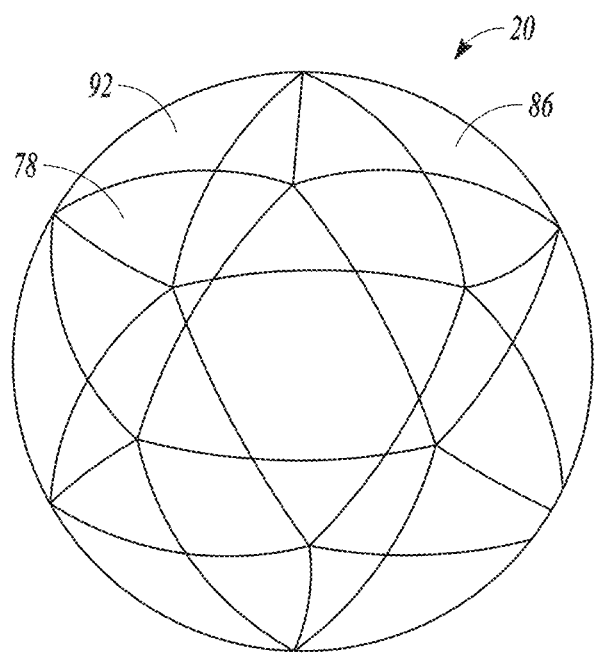
FIG. 6B shows a quasi-spherical member with a textured outer surface according to one embodiment of the present disclosure.

FIGS. 6A-B illustrate variations between the flatness of the surface of each exterior face 87 of each polygonal element 78. FIG. 6A shows a quasi-spherical member 20 having polygons 86 that have planar faces 93. FIG. 6B shows a quasi-spherical member 20 having polygons 86 that have arcuate faces 92. The arcuate face 92 can be formed with curves having a very slight radius or formed with curves having a more pronounced radius as discussed elsewhere herein.

Figure 7A:
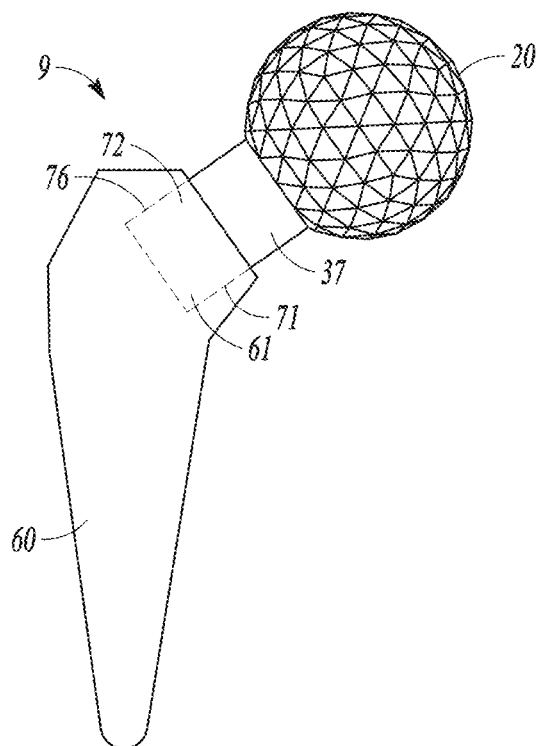
FIG. 7A shows a humeral member according to one embodiment of the present disclosure.
Figure 7B:
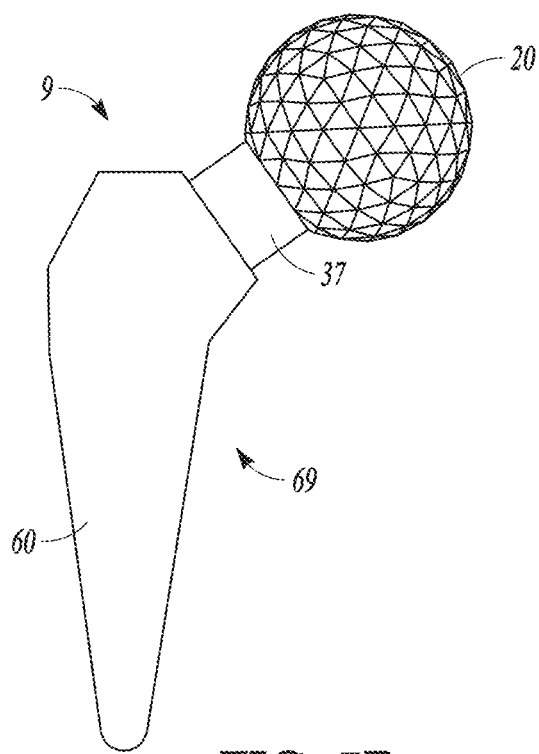
FIG. 7B shows a humeral member according to another embodiment of the present disclosure.

FIGS. 7A-B represent two configurations of an assembly 9 that includes a fixation member 60 and a quasi-spherical member 20. In FIG. 7A the assembly 9 includes at least two separate pieces. The quasi-spherical member 20 can include a connecting member 37 that is unitarily formed with the quasi-spherical member, or alternatively the connecting member can be a separately-formed piece that is subsequently connected to the quasi-spherical member using any suitable type of connection such as a taper fit or threaded connection. For example, the quasi-spherical member can include a female-type bore into which a male-type element of the connecting member is received to make a connection. Also, the fixation member 60 can include a stem cavity 76 which can receive a distal end 61 of the connecting member 37 for making a connection between the two in any suitable fashion. For example, the connection between the connecting member 37 and the fixation member 60 can be in any of the forms disclosed herein including in the form of a locking taper connection, a screw connection, a bolt connection, or a connection employing additional fasteners to facilitate making the connection. For example, the connecting member can have threads to mate with threads in the stem cavity 76. A configuration such as illustrated in FIG. 7A can allow the mixing and matching of various forms of quasi-spherical member/connecting member assemblies with various forms of connecting members and/or fixation members 60 so that a particular patient's morphology can be matched completely.

FIG. 7B illustrates an example of a monoblock assembly 69 in which the connecting member 37 is not removable from the fixation member. These examples should not be construed as limiting. For example, the connecting member 37 of FIG. 7A could be integral with the fixation member 60 instead of integral with the quasi-spherical member 20. In such a case, the quasi-spherical member 20 would have a cavity to receive a proximal end of the connecting member 37. It is also possible that the fixation member 60 and the quasi-spherical member 20 and any potential intermediate member be formed as a monoblock or otherwise formed together as a single unit.

Figure 8:
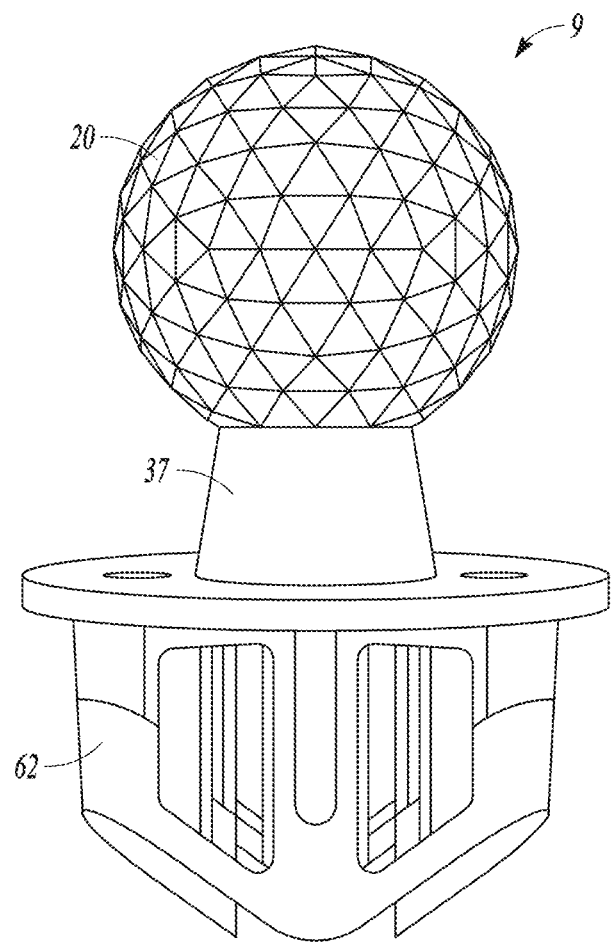
FIG. 8 shows a humeral member according to one embodiment of the present disclosure.

FIG. 8 illustrates an example of a humeral member 9 that includes a stemless member 62. The stemless member 62 could include what is considered a short stem but in any event is not inserted deep into the canal 73 of the humerus 74 and instead is anchored to more proximal portions of a humerus 74 (see FIG. 1C). While not necessary, the stemless member 62 can be connected to a distal end of a connecting member 37, which in turn can be connected at its opposite end to a quasi-spherical member 20.

Figure 9:
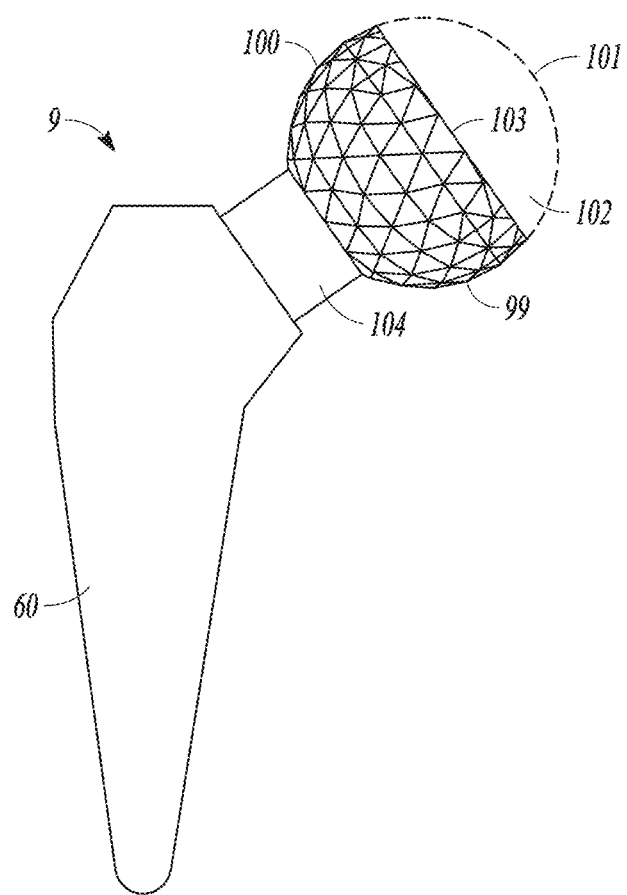
FIG. 9 shows a humeral member according to another embodiment of the present disclosure.

As discussed elsewhere herein, in some preferred forms, a textured outer surface of a male-type connector will exhibit or occupy only a portion of a particular shape such as a part of a sphere, part of an ellipsoid, etc. FIG. 9 shows a humeral member 9 according to one embodiment of the present disclosure. Member 9 includes a fixation member 60 and a male-type connector 100. A portion of the connector is shown in phantom as indicated by dashed line 101, and in this regard, it will be understood that connector 100 can have spherical or partial-spherical qualities. For example, in some forms, connector 100 will be a truncated sphere where an illustrative segment 102 of the sphere is removed or never exists as part of the connector. While the degree or amount of truncation shown in FIG. 9 may be useful in certain embodiments, it is merely illustrative of those contemplated. In this truncated version of the connector, segment 102 is defined along a single plane so as to create a proximal planar surface 103. When present, such a proximal surface can be planar or non-planar. Also, any suitable portion or percentage of such a truncated or other partial shape can be covered by a textured outer surface.

As also discussed elsewhere herein, quasi-spherical members or other male-type connectors in accordance with certain aspects of the present disclosure can incorporate a textured outer surface covering only a certain portion or percentage (e.g., between about 50% and about 90%) of the quasi-spherical member or other connector. Continuing with FIG. 9, in some other forms, one or more connector segments or other connector portions such as segment 102 will be part of the connector but will be void of a textured outer surface such as surface 99 or will have a lesser-textured, differently-textured, etc. outer surface. For example, the illustrative segment 102, when present, can have a generally smooth outer surface. In this regard, while the amount or percentage of coverage by the textured outer surface 99 shown in FIG. 9 may be useful in certain embodiments, it is merely illustrative of those contemplated. Any suitable degree or percentage of coverage by a particular textured outer surface is contemplated, e.g., more than 50%, or more than 65%, or more than 75%, or more than 85%, or between about 25% and about 50%, or between about 35% and about 75%, or between about 50% and about 90%, or between about 60% and about 100% of the quasi-spherical member or other connector.

In some embodiments, a quasi-spherical member or other male-type connector in accordance with the present disclosure is incorporated into an orthopedic product that is to be driven into or otherwise received in bone, for example, as a product for attaching or securing another orthopedic device such as a bone plate or implant to bone. In some of these embodiments, the orthopedic product is a bone screw, for example, where a quasi-spherical member or other male-type connector is disposed at a location along the length of the screw such as at a location between the ends of the screw or at or near the end of a screw to form all or part of a screw head. Such products can be formed with any suitable material(s), and in some instances, will include exterior surface that encourage bone ongrowth or ingrowth, for example, including a blasted surface to encourage bone ongrowth.

Figure 10:
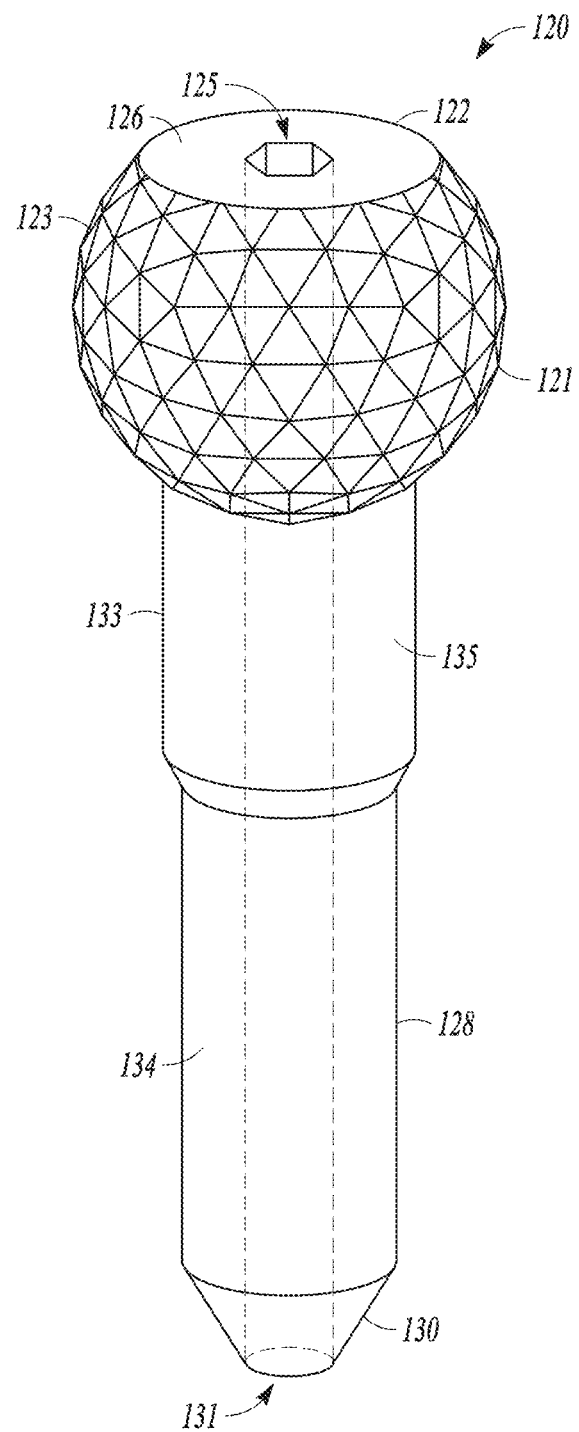
FIG. 10 shows a front view of a bone screw according to one embodiment of the present disclosure.

With reference now to FIG. 10, shown is a bone screw 120 that includes a quasi-spherical member 121 disposed at a proximal end 122 of the screw to provide a screw head 123. In this particular embodiment, a female bore 125 with a hexagonal cross section extends into the head from a proximal surface 126 of the head. Bone screw 120 also includes a shaft 128. While this sort of a quasi-spherical bone screw head can be paired with a bone screw shaft of any suitable size, shape or configuration, in this particular instance, the shaft extends distally from head 122 to a leading, distal tip 130 of the screw. A central cannula 131 continues on from female bore 125 and traverses the entire length of the screw which can be useful, for example, for placing the screw over a positioned K-wire. Bone screws and fasteners in accordance with the present disclosure can be fully or partially cannulated or non-cannulated. Cannulated regions can have any suitable wall thickness.

Continuing with FIG. 10, shaft 128 includes a proximal section 133 having a first diameter and a distal section 134 having a second diameter that is smaller than the first diameter. Bone screw and fastener shafts in accordance with the present disclosure can have constant diameters or cross sections along their lengths, or a shaft diameter or cross section can vary along its length. For example, any section of a shaft can be tapered or non-tapered. Thus, proximal section 133 and/or distal section 134 can be fully or partially tapered along its length. While not necessary to broader aspects of the disclosure, a dual- or other multi-diameter or cross section shaft can be useful in a variety of instances, for example, where shaft sections with different diameters or cross sections are intended to reside in different types or areas of bone. For example, when bone screw 120 is placed in a glenoid, this sort of dual-diameter arrangement can account for the smaller volume of bone or a minimum cross section of the bone anatomy (e.g. blade of scapula) located away from the point of entry of the screw as well as the comparatively larger volume of available bone located closer to the entry point (e.g. glenoid vault). In this regard, proximal section 133 can be considered a glenoid vault zone, and distal section 134 can be considered a glenoid blade zone of screw 120 if the screw happens to be placed in this particular anatomy.

Continuing with FIG. 10, threading 135 (not shown for clarity reasons) which can have a consistent screw pitch extends along both the proximal and distal sections of the shaft. Bone screws and fastener shafts in accordance with the present disclosure can be fully or partially threaded or non-threaded. Any suitable threading can be employed, and a screw or fastener can have different types of threading at different locations along a shaft. Above are just a few non-limiting examples of how a quasi-spherical member or other male-type connector in accordance with the present disclosure can be paired with a shaft of any suitable size, shape or configuration including self-drilling or self-tapping shafts.

Figure 11:
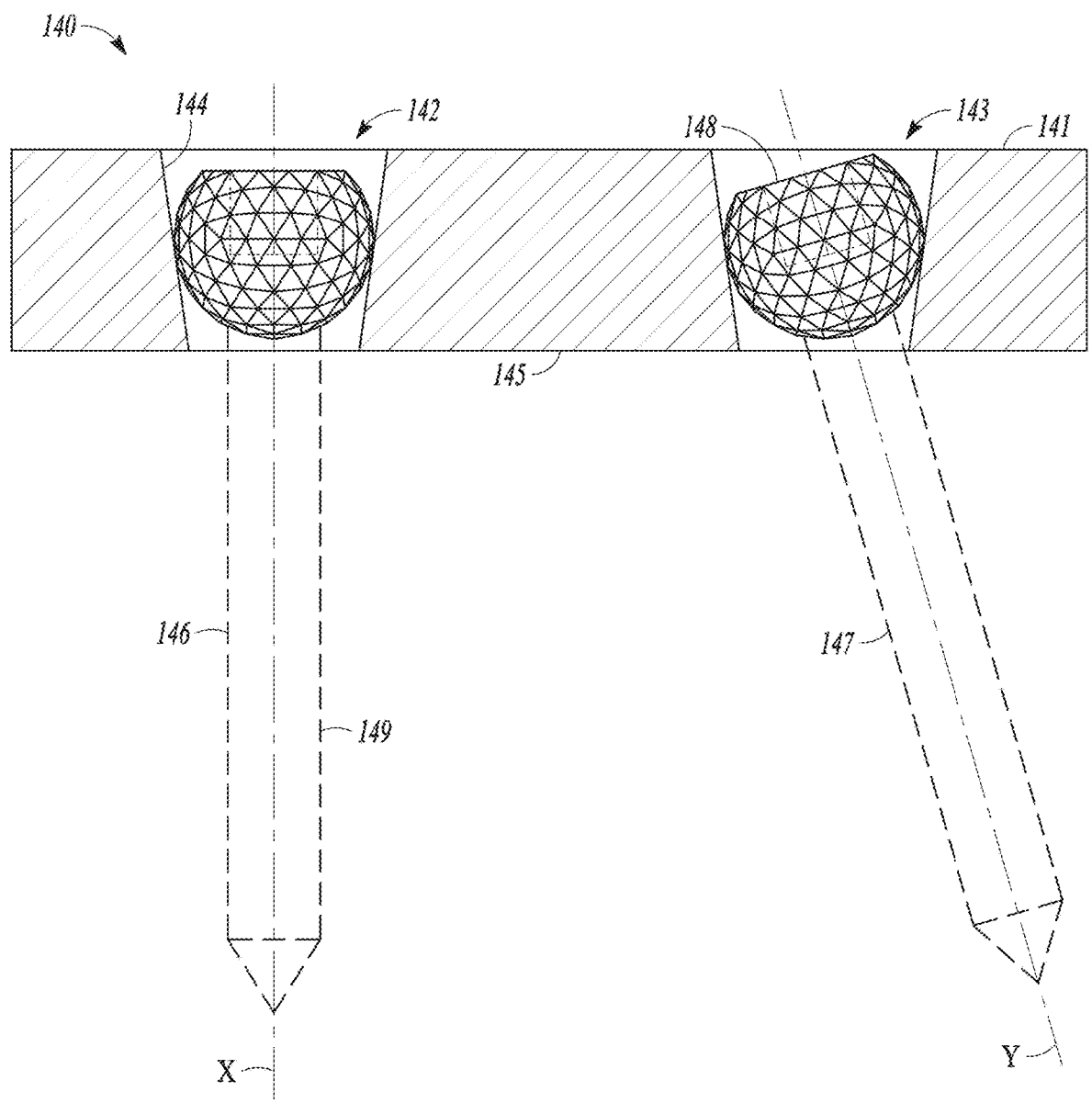
FIG. 11 shows a front view of an orthopedic assembly according to one embodiment of the present disclosure.

A quasi-spherical member or other male-type connecting member of a bone screw or other fastening-type device in accordance with the present disclosure can be used with (e.g., received and locked in a bore present in) any number of implants or other orthopedic devices disclosed elsewhere herein. These include plates (e.g., bone plates) and other non-plate orthopedic devices. One or more bone screws or other fastening-type devices in accordance with the present disclosure can be utilized in any one device. FIG. 11 is illustrative of one such device and shows, for example, how different angular positions X and Y can be achieved and maintained using connections according to aspects of the present disclosure. In particular, FIG. 11 depicts an orthopedic assembly 140 that includes an orthopedic device 141 (e.g., a bone plate or implant) that provides a first tapered female bore 142 and a second, identical tapered female bore 143 with walls 144. These particular bores have a shape of a frustum of a right circular cone. Although not necessary to broader aspects of the disclosure, the bores each extend entirely through a wall or section 145 of the device. Either bore could have any suitable size and shape. As disclosed elsewhere herein, a suitable female bore can be tapered or non-tapered and can otherwise be or incorporate any suitable three-dimensional shape, e.g., incorporating rectilinear and/or curvilinear features. Continuing with FIG. 11, assembly 140 also includes a first bone screw 146 and an identical second bone screw 147. Each screw includes a quasi-spherical head 148 and a shaft 149 extending from the head. These heads and shafts could be any combination of heads and shafts disclosed herein. In use, the leading ends of the shafts can be passed into and through the bores. In the FIG. 11 illustration, this passing occurs in a downward direction, i.e., the leading ends enter the frustoconcial bores through the larger top ends of the bores and exit the smaller bottom ends. Thereafter, the screws can be advanced (e.g., into bone) until the quasi-spherical heads are received down into the respective female bores and locked therein so as to generate the different angular positions X and Y. Based on the FIG. 11 orientation, seating can also be fully or partially accomplished by moving the bores in an upward direction relative to the heads. Although not necessary to broader aspects of the disclosure, the walls of the bores extend fully around the seated heads, e.g., with no breaks or openings in the walls that form the frustoconcial bore shapes.

Figure 12:
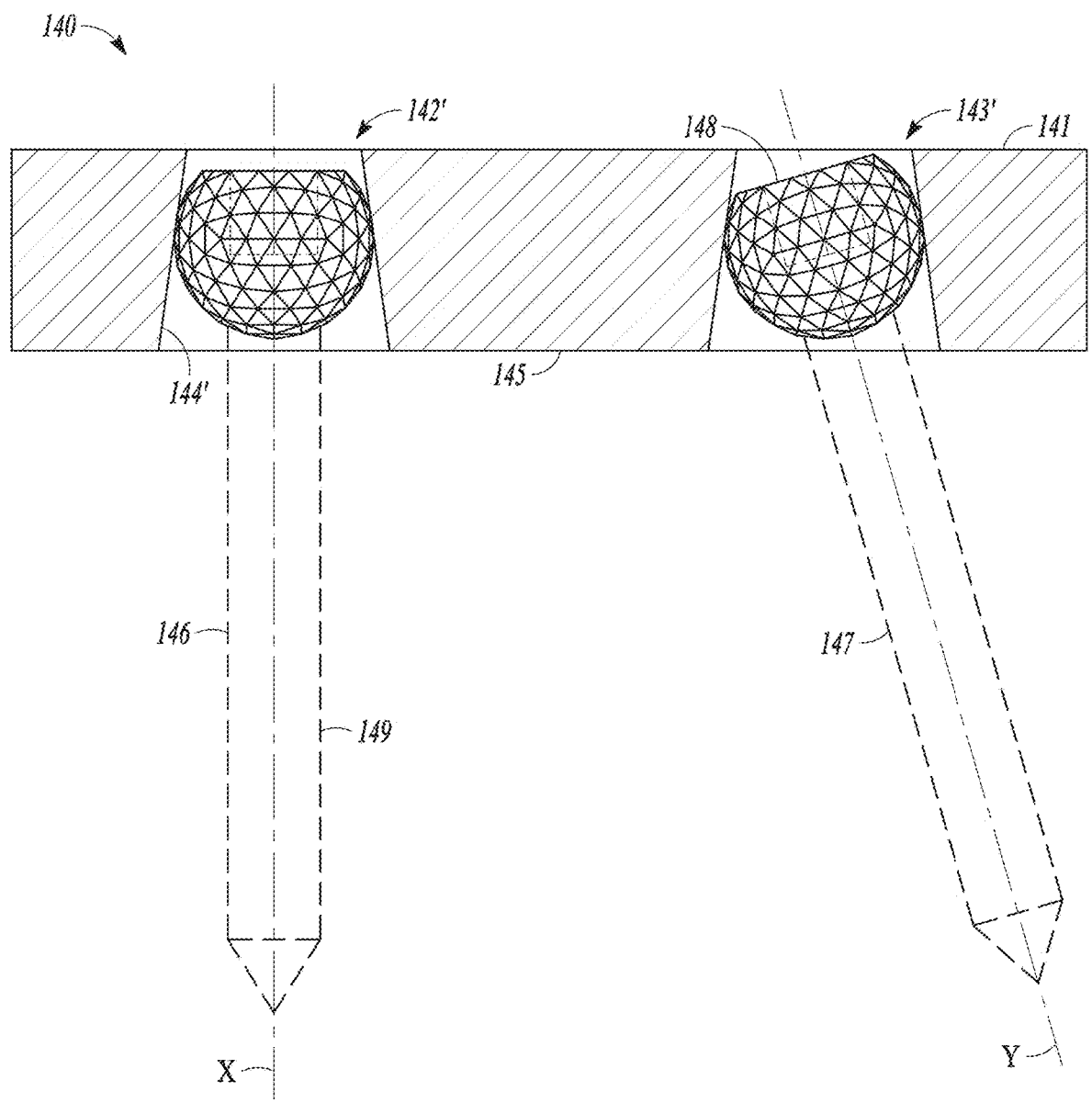
FIG. 12 shows a front view of an orthopedic assembly according to another embodiment of the present disclosure.

FIG. 12 shows a front view of an orthopedic assembly according to another embodiment of the present disclosure, and shows, for example, how different angular positions X and Y can be achieved and maintained using connections according to aspects of the present disclosure. In particular, FIG. 12 depicts an orthopedic assembly 140 that includes an orthopedic device 141 (e.g., a bone plate or implant) that provides a first tapered female bore 142' and a second, identical tapered female bore 143' with walls 144'. These particular bores have a shape of a frustum of a right circular cone. Although not necessary to broader aspects of the disclosure, the bores each extend entirely through a wall or section 145 of the device. Either bore could have any suitable size and shape. As disclosed elsewhere herein, a suitable female bore can be tapered or non-tapered and can otherwise be or incorporate any suitable three-dimensional shape, e.g., incorporating rectilinear and/or curvilinear features. Such bores could extend only partially through the wall or section, for example, as shown with the elongated bore or opening in FIG. 13C. Continuing with FIG. 12, assembly 140 also includes a first bone screw 146 and an identical second bone screw 147. Each screw includes a quasi-spherical head 148 and a shaft 149 extending from the head. These heads and shafts could be any combination of those disclosed herein. In use, the quasi-spherical heads can be received and locked in the respective female bores so as to generate the different angular positions X and Y. Based on the FIG. 12 illustration, such connections can be achieved by moving wall or section 145 in a downward direction onto the screws (e.g., by impacting the device 141) so that the heads enter the frustoconcial bores through the larger bottom ends of the bores and move a distance in the bores toward the smaller top ends until suitably locked in place. Based on the FIG. 12 orientation, seating can also be fully or partially accomplished by moving quasi-spherical heads 148 in an upward direction relative to the bores. In this regard, depending on the sizes and shapes of the various components, it is possible to make the connections with no portions of the shafts ever entering the bores. Although not necessary to broader aspects of the disclosure, the walls of the bores extend fully around the seated heads, e.g., with no breaks or openings in the walls that form the frustoconcial bore shapes. In some forms, a screw will be advanced to a desired final location in a bone before a quasi-spherical screw head is locked in a female bore of a device, for example, where a plate is impacted down onto a pre-positioned screw so that the quasi-spherical member is forcefully received and locked in the female bore.

Figure 13A:
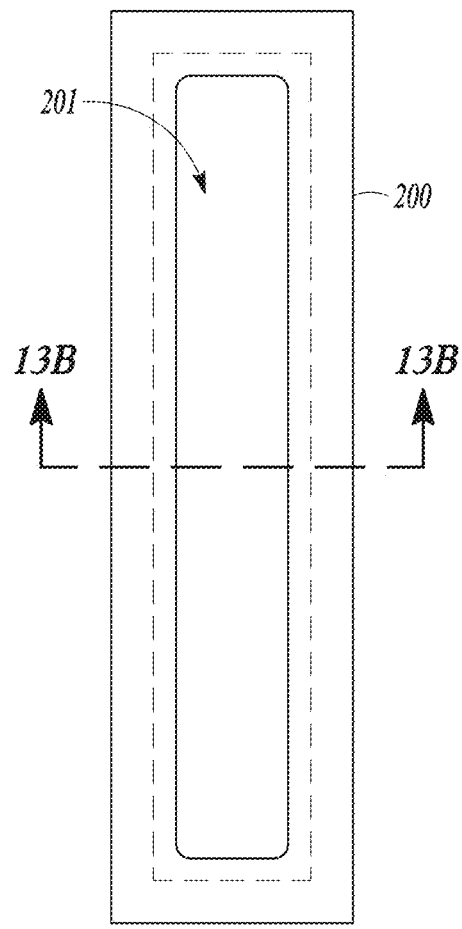
FIG. 13A shows a top view of an orthopedic plate according to one embodiment of the present disclosure.

Turning now to FIG. 13A, shown is a top view of an orthopedic plate 200 according to one embodiment of the present disclosure. From this view, plate 200 is shown to include a generally rectangular bore or opening 201. Although not necessary to broader aspects of the disclosure, the rectangular opening extends entirely through the plate, i.e., in a direction into the page based on the FIG. 13A illustration. Such an opening can be an elongated or slot-type opening of any suitable size and rectangular or non-rectangular shape. A plate or other device can incorporate any number of such openings. Illustratively, such an opening can have one dimension (e.g., rectangular slot length when viewed from the top as in FIG. 13A) that is significantly larger than another dimension (e.g., rectangular slot width) including but not limited to a first dimension that is 2 to 40, or 4 to 20, or 8 to 15 times larger than a second dimension. An elongated or slot-type opening can have curvature along its length, for example, even providing in some embodiments an annular or ring-shaped slot with no ends. Also, although the width of the opening 200 in FIG. 13A is constant along its length, it need not be. Such a slot can be a series of discernable openings or bores like those shown in FIGS. 11 and 12 which are interconnected across a plate or other device, for example, interconnected by slots or passages of a smaller width or dimension that allow interbore movement of another assembly component such as horizontal movement of a screw or fastener shaft from one bore to another along a plate or other device before the screw or fastener is ultimately locked in place in a particular bore. Any such elongated or slot-type opening can be part of any plate or non-plate orthopedic device in accordance with the present disclosure.

Figure 13B:
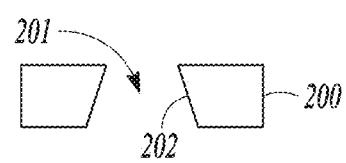
FIG. 13B is a cross-sectional view taken along view line 13B-13B from FIG. 13A.

FIG. 13B shows a cross-sectional view taken along view line 13B-13B from FIG. 13A, and it can be seen that walls 202 of the opening are angled or tapered. Based on the FIG. 13B orientation, the walls diverge moving from top to bottom so that the top end of the opening 201 is smaller than the bottom end of the opening. Based on the FIG. 13B illustration, a connection with a quasi-spherical member or other male-type connector in accordance with the present disclosure can be achieved by moving plate 200 in a downward direction onto the quasi-spherical member (e.g., which forms all or part of a screw head) so that the quasi-spherical member enters the opening through the larger bottom end of the opening and moves a distance in the opening toward the smaller top end until suitably locked in place. Alternatively, the plate could be flipped over from what is shown in FIG. 13B, and a leading tip of a screw could be passed into and through the opening, and the screw could be advanced until a quasi-spherical head of the screw is locked into the opening.

That such openings can have an elongated or slot-type shape allows a quasi-spherical member such as that of the screw shown in FIG. 10, prior to being locked in place, to be moved to different relative positions along the length of a slot or other opening. For example, when viewing the FIG. 13A illustration, such a quasi-spherical member could be received and locked in place in the opening at or near one end of the opening, at or near the far opposite end of the opening, or anywhere in between. Although not necessary to broader aspects of the disclosure, at opposite ends of the rectangular opening, the opening 201 is tapered on three sides. Alternatively, the illustration of FIG. 13B can represent one end of plate 200 such that it is not a cross-sectional view of plate 200 but rather an end view. In this regard, a quasi-spherical member could be partially and loosely received in the opening, and the plate could be slid over a quasi-spherical member (e.g., from the side) before a connection is made. Such a configuration could be particularly useful, for example, where space is limited anatomically such as where it is not easy or possible to introduce a plate or device other than from the side. Such side openings could be located anywhere on a plate or other device.

Figure 13C:
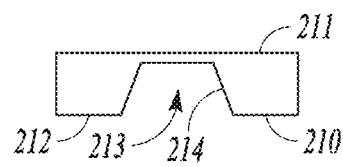
FIG. 13C shows part of an orthopedic plate according to another embodiment of the present disclosure.

FIG. 13C shows part of an orthopedic plate 210 according to another embodiment of the present disclosure. Plate 210 includes a top surface 211 and bottom surface 212. This plate is similar to that shown in FIG. 13B except that it includes an opening 213 which extends only partially through the plate, and in this regard FIG. 13C represents a cross-sectional view of the plate taken from a similar vantage point as the cross-sectional view in FIG. 13B. In particular, opening 213 extends into the plate from bottom surface 212, and walls 214 of the opening converge moving toward the top surface 211 of the plate. Alternatively, the illustration of FIG. 13C can represent one or both ends of plate 210 such that it is not a cross-sectional view of plate 210 but rather an end view. In this regard, a quasi-spherical member could be partially and loosely received in the opening, and the plate could be slid over a quasi-spherical member (e.g., from the side) before a connection is made. Such a configuration could be particularly useful, for example, where space is limited anatomically such as where it is not easy or possible to introduce a plate or device other than from the side. Such side openings could be located anywhere on a plate or other device.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An orthopedic assembly comprising:
   a bone plate that includes a non-threaded bore having a bore axis extending therethrough; and
   a quasi-spherical member including an elongate element extending therefrom along a longitudinal axis, the quasi-spherical member positionable in the bore in a plurality of different angular orientations of the longitudinal axis relative to the bore axis, wherein the quasi-spherical member is non-threaded and includes a textured outer surface for contacting walls of the bore;
   wherein portions of the textured outer surface of the quasi-spherical member are deformable upon forcible contact with the walls of the bore for fixing the position of the quasi-spherical member relative to the position of the bone plate in each of the different angular orientations; and
   wherein the textured outer surface includes at least one of a plurality of generally planar faces, a plurality of surface elements with polygonal perimeters, or a three-dimensional tessellation incorporating polygonal surfaces.

2. The orthopedic assembly of claim 1, wherein the quasi-spherical member is part of a bone screw.

3. The orthopedic assembly of claim 2, wherein the elongate element is a threaded shaft of the bone screw and the quasi-spherical member forms a head of the bone screw.

4. The orthopedic assembly of claim 3, wherein the bore extends entirely through the bone plate, and wherein the threaded shaft is receivable in the bore in advance of the quasi-spherical member.

5. The orthopedic assembly of claim 1, wherein the textured outer surface covers from about 50% to about 80% of the quasi-spherical member.

6. The orthopedic assembly of claim 1, wherein the bore includes a tapered bore segment for contacting the textured outer surface of the quasi-spherical member when the quasi-spherical member is positioned in the bore of the bone plate for immovably fixing the orientation of the quasi-spherical member relative to the bone plate.

7. The orthopedic assembly of claim 6, wherein the bore extends entirely through the bone plate from a top side of the bone plate to a bottom side of the bone plate.

8. The orthopedic assembly of claim 7, wherein the textured outer surface of the quasi-spherical member includes a plurality of planar faces having rectilinear perimeters.

9. An orthopedic assembly comprising:
a bone plate including a top side and a bottom side, the bottom side including an opening into a non-threaded tapered bore, the tapered bore including a smooth inner wall; and
a quasi-spherical member positionable in the tapered bore for removeably locking the quasi-spherical member to the bone plate, wherein the quasi-spherical member is non-threaded and includes a textured outer surface for contacting the smooth inner wall of the tapered bore when the quasi-spherical member is positioned in the tapered bore of the bone plate for immovably fixing the orientation of the quasi-spherical member relative to the bone plate, wherein portions of the textured outer surface are deformable upon forcible contact with the smooth inner wall, and wherein the textured outer surface includes at least one of a plurality of generally planar faces, a plurality of surface elements with polygonal perimeters, or a three-dimensional tessellation incorporating polygonal surfaces.

10. The orthopedic assembly of claim 9, wherein the top side of the bone plate includes an opening into the tapered bore such that the tapered bore extends through the bone plate from the top side to the bottom side.

11. The orthopedic assembly of claim 10, wherein the opening in the top side is larger than the opening in the bottom side such that the tapered bore tapers inwardly from the top side toward the bottom side of the bone plate.

12. The orthopedic assembly of claim 10, wherein the opening in the top side is smaller than the opening in the bottom side such that the tapered bore tapers inwardly from the bottom side toward the top side of the bone plate.

13. The orthopedic assembly of claim 9, wherein the quasi-spherical member comprises a head portion of a bone fastener, the bone fastener further including a shaft portion extending from the head portion.

14. The orthopedic assembly of claim 9, wherein the tapered bore comprises a conically tapered bore.

15. The orthopedic assembly of claim 9, wherein the textured outer surface covers from about 50% to about 80% of the quasi-spherical member.

16. The orthopedic assembly of claim 9, wherein the quasi-spherical member comprises a truncated sphere with at least one planar surface.

17. The orthopedic assembly of claim 9, further comprising:
a second opening into a second tapered bore in the bottom side of the bone plate, the second tapered bore including a smooth inner wall; and
a second quasi-spherical member positionable in the second tapered bore for removeably locking the second quasi-spherical member to the bone plate, wherein the second quasi-spherical member includes a textured outer surface for contacting the smooth inner wall of the second tapered bore when the second quasi-spherical member is positioned in the second tapered bore of the bone plate.

18. An orthopedic assembly comprising:
a bone plate including a top side, a bottom side, and a non-threaded tapered bore extending entirely through the bone plate from the top side to the bottom side, the tapered bore including a smooth inner wall; and
a bone fastener including a quasi-spherical head and a threaded shaft, the threaded shaft receivable in the tapered bore in advance of the quasi-spherical head and the quasi-spherical head positionable in the tapered bore, wherein the quasi-spherical head is non-threaded and includes a textured outer surface for contacting the smooth inner wall of the tapered bore when the quasi-spherical head is positioned in the tapered bore of the bone plate for immovably fixing the orientation of the quasi-spherical head relative to the bone plate, wherein portions of the textured outer surface are deformable upon forcible contact with the smooth inner wall, and wherein the textured outer surface includes at least one of a plurality of generally planar faces, a plurality of surface elements with polygonal perimeters, or a three-dimensional tessellation incorporating polygonal surfaces.

* * * * *